US012102490B2

(12) United States Patent
Paitel et al.

(10) Patent No.: US 12,102,490 B2
(45) Date of Patent: *Oct. 1, 2024

(54) SYSTEM AND METHOD FOR VIEWING A SUBJECT

(71) Applicant: Medtronic Navigation, Inc., Louisville, CO (US)

(72) Inventors: Yvan Paitel, Louisville, CO (US); Neil F. Straka, Boulder, CO (US); Timothy J. Schaewe, Nederland, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/194,846

(22) Filed: Apr. 3, 2023

(65) Prior Publication Data

US 2023/0248469 A1   Aug. 10, 2023

Related U.S. Application Data

(63) Continuation of application No. 16/861,334, filed on Apr. 29, 2020, now Pat. No. 11,628,037.

(51) Int. Cl.
| | |
|---|---|
| *G06F 3/00* | (2006.01) |
| *A61B 34/20* | (2016.01) |
| *A61B 90/00* | (2016.01) |
| *G02B 21/00* | (2006.01) |
| *G06F 3/01* | (2006.01) |
| *G06T 19/00* | (2011.01) |

(52) U.S. Cl.
CPC .............. *A61B 90/37* (2016.02); *A61B 34/20* (2016.02); *G02B 21/0012* (2013.01); *G06F 3/012* (2013.01); *G06T 19/006* (2013.01); *A61B 2034/2055* (2016.02); *A61B 2090/365* (2016.02); *A61B 2090/373* (2016.02)

(58) Field of Classification Search
CPC ...... A61B 2034/107; A61B 2034/2051; A61B 2034/2055; A61B 2034/2059; A61B 2034/2063; A61B 2090/365; A61B 2090/373; A61B 2090/395; A61B 34/20; A61B 34/25; A61B 90/20; A61B 90/25; A61B 90/361; A61B 90/37; G06F 3/011; G06F 3/012; G06F 3/04815; G06T 19/006; G02B 21/0012
See application file for complete search history.

(56) References Cited

U.S. PATENT DOCUMENTS

| | | |
|---|---|---|
| 6,436,054 B1 | 8/2002 | Viola et al. |
| 7,697,972 B2 | 4/2010 | Verard et al. |

(Continued)

OTHER PUBLICATIONS

U.S. Appl. No. 16/861,334, Apr. 29, 2020, Paitel, Yvan.

(Continued)

*Primary Examiner* — Insa Sadio
(74) *Attorney, Agent, or Firm* — Harness, Dickey & Pierce, P.L.C.

(57) ABSTRACT

A viewing system or imaging system is disclosed that includes optical pieces for viewing a subject. The viewing system may include features that allow an augmented mixed view through eyepieces of the viewing system. The mixed view may include graphical representations that are acquired or determined with information separate from the viewing system.

18 Claims, 11 Drawing Sheets

(56) References Cited

U.S. PATENT DOCUMENTS

| | | | |
|---|---|---|---|
| RE44,305 | E | 6/2013 | Foley et al. |
| 8,644,907 | B2 | 2/2014 | Hartmann et al. |
| 8,842,893 | B2 | 9/2014 | Teichman et al. |
| 2002/0120424 | A1 | 8/2002 | Hauger et al. |
| 2004/0199072 | A1 | 10/2004 | Sprouse et al. |
| 2005/0059894 | A1 | 3/2005 | Zeng et al. |
| 2013/0176336 | A1 | 7/2013 | Hannula |
| 2013/0266123 | A1 | 10/2013 | Yoshida et al. |
| 2014/0078175 | A1 | 3/2014 | Forutanpour et al. |
| 2017/0085855 | A1 | 3/2017 | Roberts et al. |
| 2017/0325901 | A1* | 11/2017 | Harlev ............... A61B 34/10 |
| 2018/0368656 | A1 | 12/2018 | Austin et al. |
| 2019/0327394 | A1* | 10/2019 | Ramirez Luna ....... H04N 23/51 |
| 2019/0328460 | A1 | 10/2019 | Ronen et al. |
| 2019/0328461 | A1 | 10/2019 | Kemp et al. |
| 2021/0338367 | A1 | 11/2021 | Paitel et al. |
| 2021/0343048 | A1 | 11/2021 | Paitel et al. |

OTHER PUBLICATIONS

International Search Report and Written Opinion regarding International Application No. PCT/US2021/029389, dated Aug. 13, 2021.

Invitation to Pay Additional Fees regarding International Application No. PCT/US2021/029409, dated Sep. 15, 2021.

Drouin Simon et al: "IBIS: an OR ready open-source platform for image-guided neurosurgery", International Journal of Computer Assisted Radiology and Surgery, Springer, DE, vol. 12, No. 3, Aug. 31, 2016, pp. 363-378, XP036159442, ISSN: 1861-6410, DOI: 10.1007/S11548-016-1478-0 [retrieved on Aug. 31, 2016].

Cabrilo Ivan et al: "Augmented reality in the surgery of cerebral arteriovenous malformations: technique assessment and considerations", Acta Neurochirca, vol. 156, No. 9, Sep. 1, 2014, pp. 1769-1774, XP055827558, At ISSN: 0001-6268, DOI: 10.1007/s00701-014-2183-9 URL: https://link.springer.com/content/pdf/10.1007/s00701-014-2183-9.pdf.

Munzer Bernd et al: "Content-based processing and analysis of endoscopic images and videos: A survey", Multi Media Tools and Applications, Kluwer Academic Publishers, Boston, US, vol. 77, No. 1, Jan. 11, 2017, pp. 1323-1362, XP036403706, ISSN: 1380-7501, DOI: 10.1007/S11042-016-4219-Z.

Megali Giuseppe et al: "EndoCAS navigator platform: a common platform for computer and robotic assistance in minimally invasive surgery", International Journal of Medical Robotics and Computer Assistedsurgery, vol. 4, No. 3, Sep. 1, 2008, pp. 242-251, XP055827122, GB ISSN: 1478-5951, DOI: 10.1002/rcs.203.

International Search Report and Written Opinion regarding International Application No. PCT/US2021/029409, dated Nov. 8, 2021.

International Preliminary Report on Patentability regarding International Patent Application No. PCT/US2021/029389, dated Nov. 10, 2022.

International Preliminary Report on Patentability regarding International Patent Application No. PCT/US2021/029409, dated Nov. 10, 2022.

European Communication from the European Patent Office for related European Application No. 21726489.4 dated Jun. 25, 2024, 6 pages.

* cited by examiner

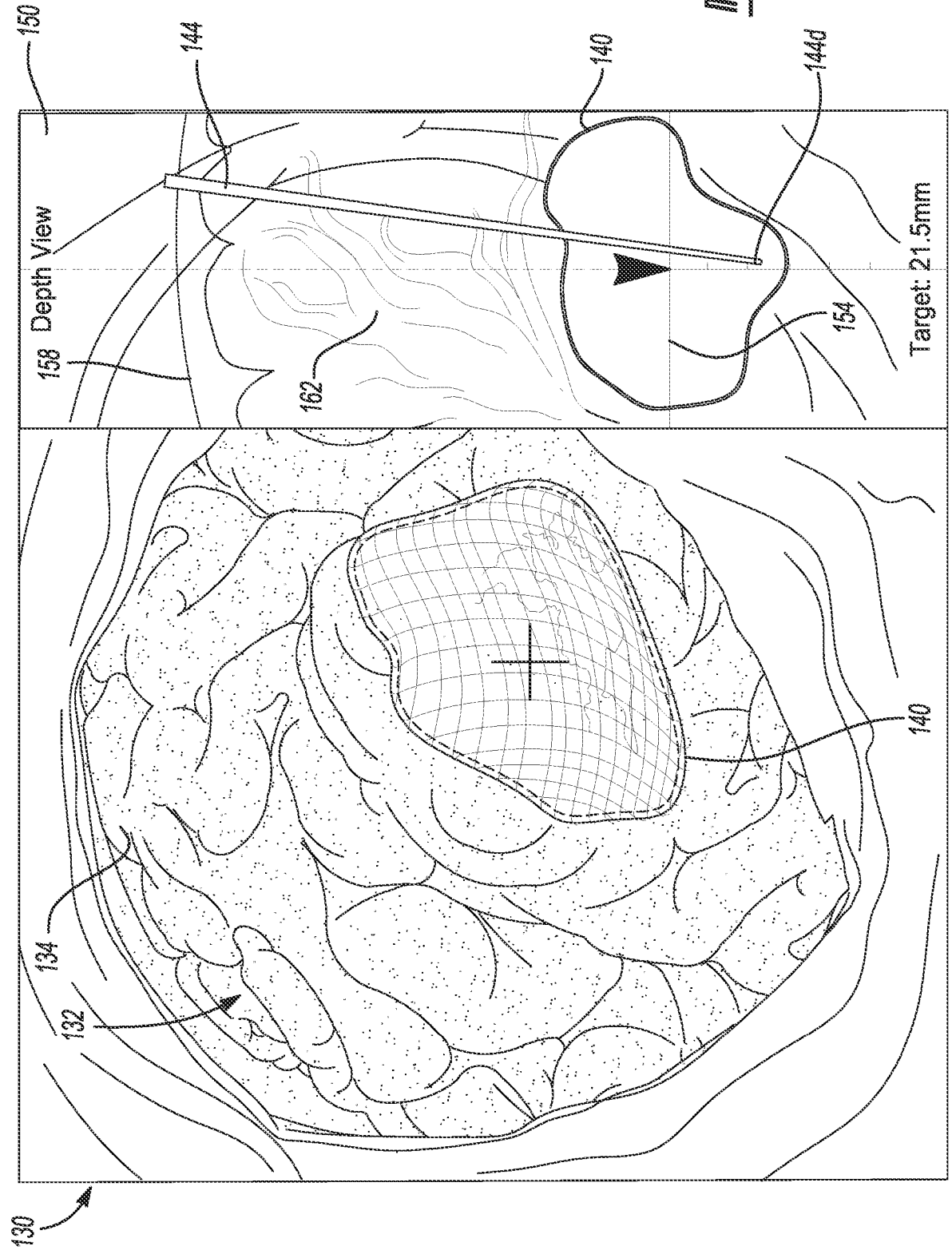

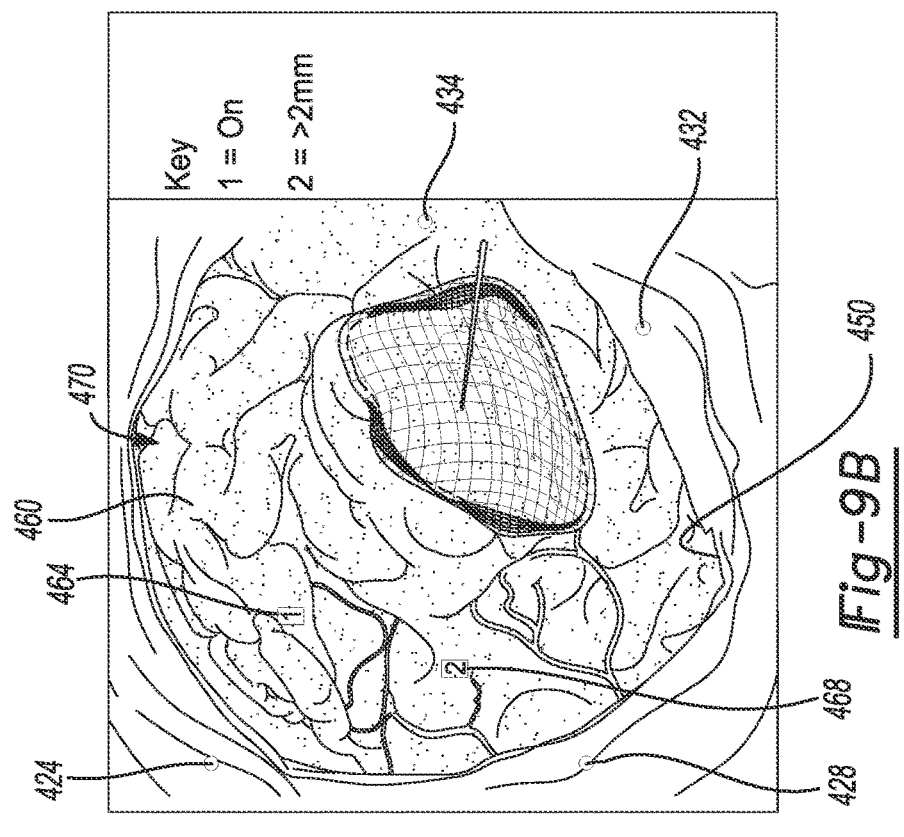

SYSTEM AND METHOD FOR VIEWING A SUBJECT

CROSS-REFERENCE TO RELATED APPLICATIONS

This is a continuation application of U.S. Ser. No. 16/861,334, filed Apr. 29, 2020, which includes subject matter related to U.S. patent application Ser. No. 16/861,328 filed Apr. 29, 2020 and Ser. No. 18/168,296 filed Feb. 13, 2023. The entire disclosures of each of the above applications are incorporated herein by reference.

FIELD

The present disclosure relates to visualization, and particularly to a mixed visualization during a procedure.

BACKGROUND

This section provides background information related to the present disclosure which is not necessarily prior art.

During a procedure, such as a procedure viewing the internal portions of an object, various visualization and viewing systems may be used. For example, a microscope or visualization enhancement system may be used to view internal components of an object. The viewing system generally allows for a direct and magnified viewing of the internal component through various optical lenses during a procedure.

SUMMARY

This section provides a general summary of the disclosure, and is not a comprehensive disclosure of its full scope or all of its features.

A visualization system may include a microscope or other direct visualization system. The direct visualization system may include an optical pathway that may include various optical lenses, such as magnification, focusing, and the like. The lenses may be used to transmit light from an object to a viewing area that may include an eyepiece. A user of the microscope, which may define a focal plane, may view the image through the eyepiece. The user may view or see the focal plane (also referred as a viewing plane) through the eyepiece.

In a viewing area, the user may view the object on which the procedure is performed. In the viewing area, a display may be provided that displays the transmitted light from a work area for viewing by a user. Various augmentations may be provided in the viewing area and/or prior to the viewing area to augment the view of the object. The view provided to the user and/or view by the user may be a mixed view that includes both a live view or image of the subject and other superimposed to displayed features (e.g. graphical representation of hidden or obstructed objects).

In various embodiments, portions may be highlighted in the view, graphical representations of various items or portions and/or recalled and displayed visualizations may be overlaid on the current view of the object. In various embodiments, for example, projections may be made into the optical path that illustrate or provide an augmented reality (AR), also referred to as a mixed view, that may be viewed by the user. Thus, the user may view both a real time display or view (e.g. live view) of the object while also viewing an augmented or additional portion (e.g. a graphical representation) displayed relative to the real time image.

In various embodiments the object may be a living or non-living object, and may include a patient.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a live view and selected information provided relative to the live view with the microscope system;

FIG. 9A is a live view and mixed superimposed image through the microscope system;

FIG. 9B is a mixed live view and superimposed graphical representation view of the microscope system;

Corresponding reference numerals indicate corresponding parts throughout the several views of the drawings.

DETAILED DESCRIPTION

Example embodiments will now be described more fully with reference to the accompanying drawings.

A procedure may be performed in a selected location, such as in a surgical suite 20. It is understood, however, that a surgical suite may be any appropriate selected procedure room and a surgical suite is merely exemplary. Further, it is understood that any appropriate procedure may be performed relative to a living or non-living subject. For example, a procedure may occur on a complex machinery system where disassembling the entire system is undesired. Further, the procedure may occur on a living subject, such as a human subject, for selected purposes.

Figure 1:
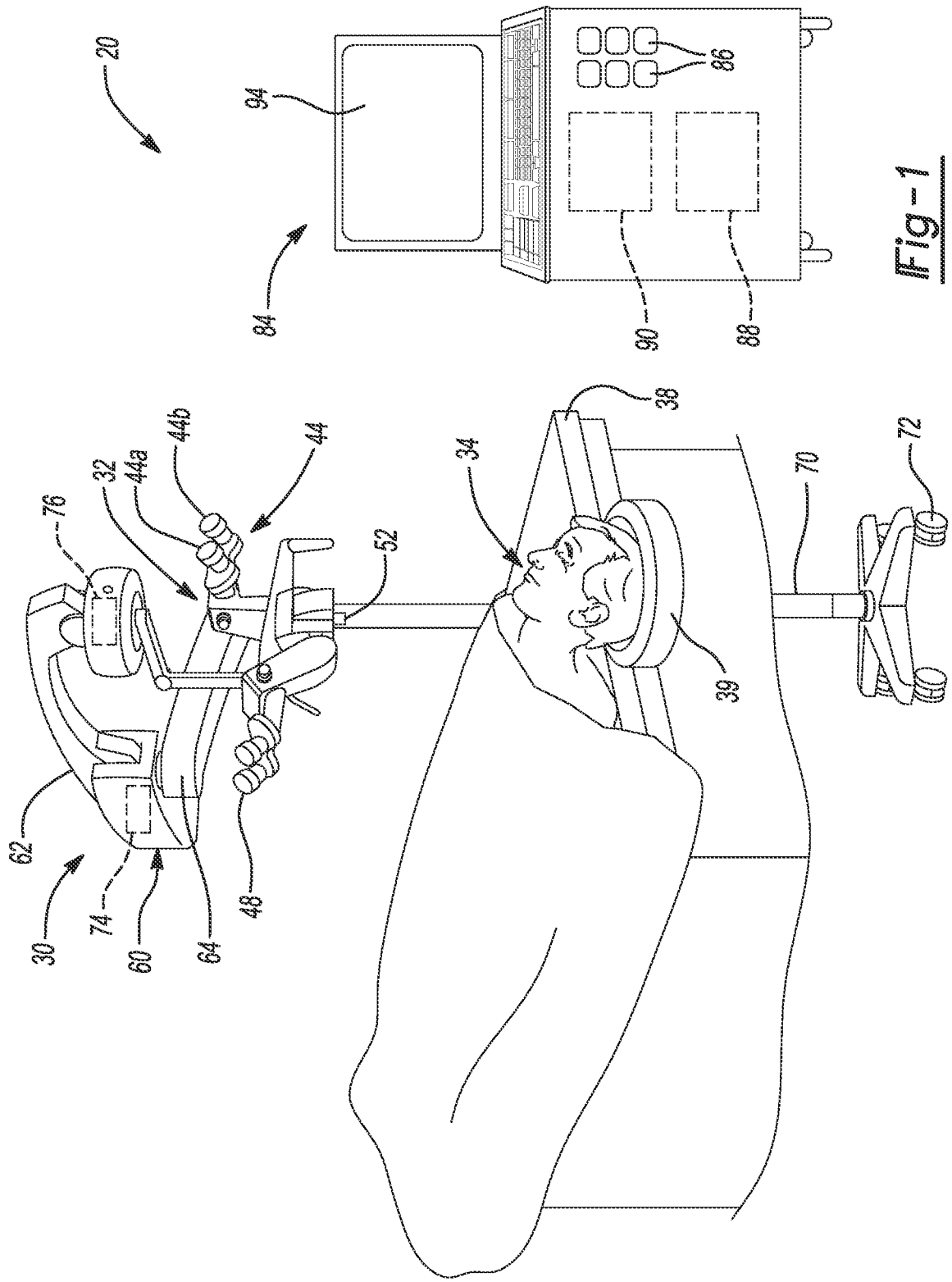
FIG. 1 is an environmental view of a microscope system, according to various embodiments.
Figure 2:
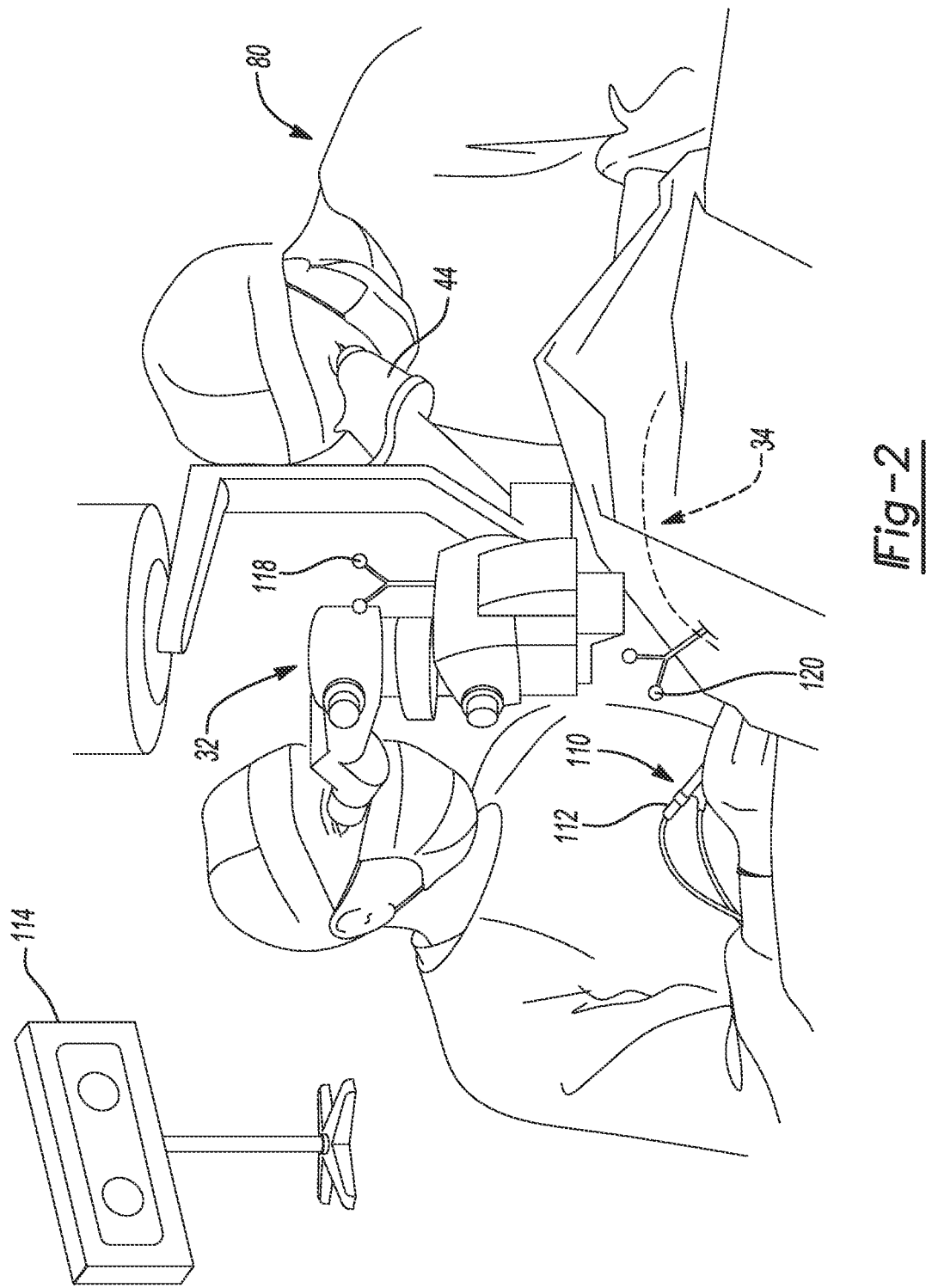
FIG. 2 is a detailed view of a microscope system and selected users.

With reference to FIGS. 1 and 2, in various embodiments, a surgical suite may include a viewing or optical system, such as a surgical microscope system 30. The viewing system 30, which may also be referred to as a microscope herein, may include various components for performing a procedure on a subject 34. In various embodiments, the subject 34 may be held or positioned with a support, such as a patient support or operating table 38. The surgical microscope system 30 may include a microscope component also referred to as a head assembly 32 that may include one or more viewing ports or portals, also referred to as eyepieces or ocular lenses or units 44. The microscope 30 may be a binocular microscope such that a plurality, such as two ocular units, 44a, 44b, may be provided. Additionally more than one ocular units, such as a second or auxiliary ocular unit 48, which may also be stereoscopic or binocular, may be provided. Thus, more than one individual may view the same portion of the subject 34 simultaneously and view the subject in three-dimensions due to the binocular system 44, 46.

During a selected procedure, the subject 34 may be viewed through the eyepieces 44. Positioned near or moved near the subject 34, and also formed or connected to the head portion 32, may be one or more objective lenses 52. Therefore, the objective lens 52 may be positioned near the subject 34. The object lens 52 gathers the light from the subject 34 (e.g. reflected light) and allows transmission through the head portion 32. Various lens systems in the microscope 30 may, therefore, allow for an enhanced or enlarged view of the subject 34 between the objective lens 52 and the eyepieces 44.

In various embodiments, the surgical microscope 30 may include the microscope head component 32, which may include optical components such as eyepieces 44 and lens 52, and one or more arms or support members 60. The support members may include a first support arm 62 and a second support arm 64. The second support arm 64 may be mounted to a floor or main support 70 which may be fixed in a selected location and/or be mobile, via one or more wheels 72. It is further understood that the wheels 72 may be locked in a selected pose to fix the microscope 30 in a selected pose relative to the subject 34.

In various embodiments, one or more motors may be provided in and/or to move the one or more arms 60. For example, a first motor 74 may be provided to move the first arm 62 relative to the second arm 64 and a second motor 76 may be provided to move the head 32 relative to the first arm 62. Thus, the head 32, including the lens 52, may be moved in a selected manner relative to the support member 70 and/or the subject 34. The motors 74,76 may be appropriate motors, such as electric motors that may include encoders and/or operate with encoders to determine precise movement (e.g. with a selected amount of movement or positional determination error that may be within a selected tolerance, such as less than about 5 millimeters (mm), less than about 1 mm, less than about 0.1 mm, etc.). Motors 74, 786 may include DC stepper motors or other appropriate motors.

In various embodiments the motors 74, 76 may be controlled by a user 80. In addition, one or more control or processor modules or system 84 may be provided to control the selected motors 74, 76 and/or other components of the surgical microscope 30. For example, the processor system 84 may include one or more inputs 86 to control the microscope portion 32 for selected movements and/or storing selected poses of the microscope 32. Accordingly, after storage of selected poses of the microscope 32, the microscope 32 may be moved back or returned to the selected poses, such as relative to the support member 70, for viewing after a selected procedure of after a selected passage of time.

The processor system 84, therefore, may include a processor module 88 and one or more memory modules 90. The processor 88 and the memory 90 may be any appropriate processor or memory, such as those discussed further herein. Further, one or more display devices, such as an LCD or LED display device 94 may be provided for viewing various inputs, statuses, and/or images viewed with the microscope 32.

The user 80 may use or operate the microscope system 32 to perform a procedure on the subject 34 with one or more instruments 110. The instruments 110 may include one or more tracking devices 112 that may be tracked with one or more localization systems 114. The localization systems 114 may include one or more of an optical, electromagnetic, acoustic, or other localization systems that may be used to track tracking devices and the portions to which the tracking devices area mounted. Generally, the localization system 114 may be used to track a location of the tracking device 112 that may be associated with the instrument 110 relative to the subject 34. Associated with the surgical microscope system 30, including and or directly to the head component 32, may also be a microscope or viewer tracking device 118. The subject 34 may also have a tracking device 120 attached thereto. Therefore, the instrument 110, the subject 34, and the microscope 32 may all be tracked relative to one another, including simultaneously, with the respective tracking devices and the tracking localizer and system 114. Other appropriate pose systems may also be used to assist and/or perform tracking such as tracking devices associated with the motors for moving the microscope 32 and fixation of the subject 34 at a known pose. As discussed above, encoders may be included with the motors 74, 76 and/or that the joints of the members 62, 64 for determinate movement and/or pose of the microscope 32 such as in a robotic system or microscope. In various embodiments, the pose of the lens 52 relative to the subject 34 may be most relevant for viewing various features relative to the subject 34. As discussed herein, a pose of a portion (e.g. the microscope 32, subject 34, and/or instrument 110) may include all position and orientation information, e.g. six degree of freedom, such as translational (x,y,z) coordinates and orientation (yaw, pitch, roll) coordinates.

In various embodiments, therefore, the pose of the instrument 110 may be illustrated as a graphical representation superimposed on a view through the eyepieces 44 of the microscope 32. Various tracking systems that are able to register prior acquired image or other data to a subject include the StealthStation® S8 surgical navigation system sold by Medtronic Navigation having a place of business in Colorado and/or systems disclosed in U.S. Pat. App. Publication No. 2019/0328461, published Oct. 31, 2019, incorporated herein by reference.

Registration may include registering prior acquired information (such as image data) to the subject 34 for determining a pose relationship of the prior acquired image data to the subject 34 in real time. Similar, the tracking systems may be used to illustrate the pose of tracked systems to the prior acquired information.

In various embodiments, the system including the localizer 114 may incorporate various portions or systems, such as those disclosed in U.S. Pat. Nos. RE44,305; 7,697,972; 8,644,907; and 8,842,893; U.S. Pat. App. Pub. No. 2004/0199072, and U.S. Pat. App. Pub. No. 2019/0328460 all incorporated herein by reference. The localizer 114 of a navigation system may be used to track a pose of an object, as discussed herein. The pose may then be displayed for viewing by the user 80, as also discussed herein. Also, tracking information, including information regarding the magnetic fields sensed with the tracking devices and/or optical signals may be delivered via a communication system to selected portions of the microscope system 20, such as the processor 88. The communication may be wired or wireless using appropriate systems.

Image data, in addition to the live view, as discussed herein, may be acquired such as with one or more of the imaging systems prior to and/or during a surgical procedure for displaying an image or portion thereof for viewing by the user 80 through the eyepieces 44. The additional information or data may be viewed by the user 80 with the live view, as discussed herein.

A navigation or tracking domain or volume generally defines a navigation space or patient space in which objects may be moved that are tracked, such as with the localizer 114. Due to the tracking devices 112, 118, 120 the various portions may be tracked relative to one another. The navigation volume or patient space may be registered to an image space defined by the additional information (e.g. prior acquired image or selected image) of the subject 34. The registration allows for illustrating and displaying determined positions of various objects relative to one another and/or the image space. In various embodiments, registration may occur by determining identical points or portions (e.g. registration points or landmarks) in the image space and the navigation space. The registration points may be natural (e.g. anatomical) or artificial (e.g. fixed to the subject). Once determined in both spaces, however, a registration may be made by determining a transformation between the two spaces using the registration points. The transformation and registration may be carried out by executing instructions with an appropriate processor, such as the processors 88. Registration of the patient space to the image space and determining a position of a tracking device, such as with the tracking device 118, relative to a DRF, such as the DRF 120, may be performed as generally known in the art, including as disclosed in U.S. Pat. Nos. RE44,305; 7,697,972; 8,644,907; and 8,842,893; and U.S. Pat. App. Pub. No. 2004/0199072, all incorporated herein by reference.

With continuing reference to FIGS. 1 and 2 and additional reference to FIG. 3 a view through the eyepieces 44 may include a display or image 130. The image 130 may include or display various information such as a direct or live view, also referred to as a real time view, 132 of a selected portion of the subject, such as a brain 134. The live view 132 may be viewed directly through the microscope 32 such as a general direct light transmission through the eyepieces 44 for viewing by the user 80. The live view may be of a viewing area or procedure area at a viewing plane. The viewing plane is generally understood to be the area or plane at which the microscope is focused and the user 80 may view through the eyepiece 44. The live view may be a current or real time view.

In addition to the live view 132 in the view 130, additional information may be superimposed onto the live view 132 and/or displayed near or adjacent the live view due to, for example, tracking of the subject 34 with the subject tracking device 120 and/or the microscope 32 with the microscope tracking device 118. In various embodiments, one or more targets may be determined. The one or more targets may be referred to herein as one or a target, but it is understood that more than one target may be determined. Also, the target may be any appropriate portion, such as an anatomical feature, an anomaly, etc. and/or a selected location (e.g. a volume include a selected specific feature, such as a tumor). For example, acquired image data, such as MRI image data, may be used to identify a tumor as the target and an outline of a tumor that may be displayed as a target graphical representation 140. In addition, the instrument 110 may be illustrated as an instrument illustration or graphical representation (also referred to as an icon) 144 due to the tracking of the subject 34 and the instrument 110. Thus, a pose of the instrument 110 may be viewed directly with the microscope 32 through the eyepieces 44 and/or a representation of the instrument 110 may be illustrated as the graphical representation 144.

As illustrated in FIG. 3, through the eyepiece 44, in addition to the live image 130, an additional overlay or graphical view 150 may be displayed. The overlay 150, or any appropriate graphical representation, may be opaque, transparent, or at least partially transparent. In a partially transparent overlay, the live image may be viewable through the overlay 150. The mixed or augmented view 150 may include additional or selected information such as the graphical representation of the instrument 144 and/or the representation of the tumor or selected target 140. The augmented view 150 may additionally include information, such as a depth line or indication 154 from a surface 158. The plane or surface representation 158 may be a surface of the brain 132, or other selected portion of the subject 34 in the live view 130. The surface may also be a view plane through the eyepiece 44

As discussed above, the pose of the subject 34 may be determined with the subject tracking device 120 which may include a pose of selected portions of the subject, such as a surface of the brain 132. Also, the subject 34 may be fixed in a selected position with a holding or fixation device, such as a head clamp 39. Therefore, the outer or surface line 158 may be determined and illustrate the augmented view 150. The instrument 110 may be tracked with the tracking device 112 and illustrated by the graphical representation 144 in the augmented view 150.

Additionally, information regarding the subject 34, such as fiber tractography or tractography representations 162 may also be displayed in the augmented view 150 relative to the live view 130 of the subject 34. The fiber tracts may be determined with additional, including, previously acquired information. The prior or additionally acquired information may be registered to the subject due to the tracking of the subject 34, as discussed above. Further, the pose of the microscope 32 may be known relative to the subject 34. Thus, the additional registered information (e.g. tractography) may be displayed in the mixed view. Thus, the user 80 may view the subject 34 through the microscope 32 and view additional information, in addition to the live view 130 of the subject 34, including the augmented view 150. The outline of the target 140, a graphic representation of the instrument 144, and selected depth or target information may also be displayed. This allows the user 80 to view a depth or three-dimensional representation of the selected target at its location within the subject through the microscope view ports 44 simultaneously with a live view. The augmented image 150 may allow for the user 80 to better understand a representation of the view or image of the subject 34 rather than viewing simply or only the live view through the microscope 32.

As discussed above the live view 130 as viewed through the eyepiece 44 allows the user 80 to directly view a live view or a current view of one or more portions of the subject 34. The additional data, such as the graphical representations of the tumor or target 154, graphical representation of the instrument 144, representation of a surface or outer extent 158, and/or tractography information 162 may be based upon various prior acquired image data and/or analysis of the subject 34. The positioning of the graphical representations in the live view and/or on the additional or augmented view 150 may be based upon tracking the subject 34 with the subject tracking device 120 and the microscope 32 with the microscope tracking device 118.

The additional information may be registered to the subject 34 due to a selected registration, such as image registration, to the subject 34 as is generally understood by one skilled in the art. For example, the tracking localizer 114 may be used to track a plurality of portions, such as the subject 34 with the subject tracking device 120 and/or the microscope 32 with the microscope tracking device 118. One or more selected processors, such as the processor 88, may be used to perform a registration of the subject space defined by the subject 34 relative to the microscope 32 and/or additional image data space. The tracking system may be one similar to the Stealth Station® Navigation System, sold by Medtronic Navigation, Inc. having a place of business in Colorado. The various navigation systems or tracking systems may be used to determine the pose of the subject 34 relative to the microscope 32 with the respective tracking devices and, therefore, determine the pose to place the graphical representations, such as the graphical representation of the instrument 144, in the augmented view 150. The augmented view may be displayed with a semi-transparent screen or plate, such as those included in the Kinevo 900 microscope, sold by Carl Zeiss Meditec AG having a place of business in Germany and/or a microscope having a screen of a selected resolution, that may be used to display the augmented view 150. Further, the user 80 may select to determine or identify graphical representations to display in the augmented view 150 such as with the inputs 86 with the microscope system. Accordingly, the user 80 may select to display or not display various items, such as the surface line 158, the selected outline 140, or other selected graphical representations.

Additionally the various graphical representations may be displayed in appropriate manners such as in two-dimensional representations, three-dimensional representations, or in changing representations such as a time varying may be based upon various information, such as gating relative to a heartbeat of the subject 34. The three-dimensional rendering may be displayed to the user 80 as a three-dimensional image due at least in part to the binocular eyepieces 44. Thus, the user 80 may view the image of the subject 34 augmented with selected graphical representations, as discussed above. Particularly the augmented view 150 may display or illustrate a depth from a selected surface, such as at the surface line 15. The augmented display may also illustrate a position or depth of the instrument 110, such as with the graphical representation of 144, including viewing a distal tip 144d of the instrument 110.

Figure 4A:
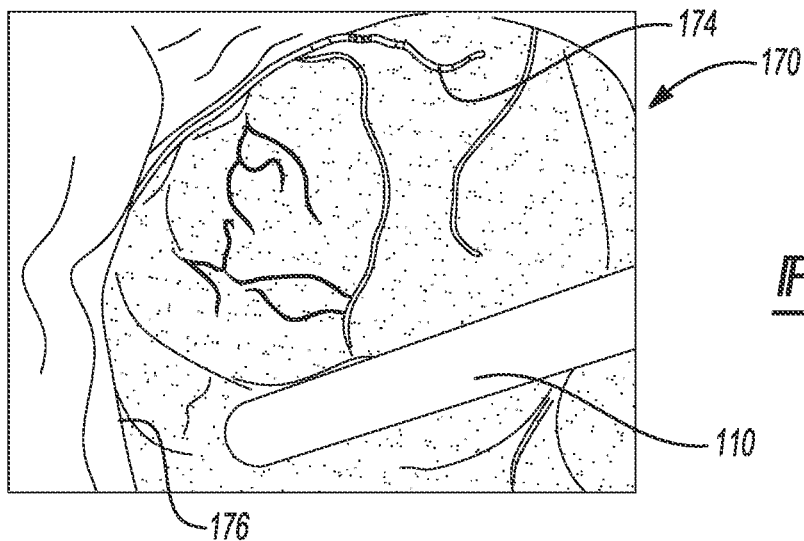
FIG. 4A is a live view through a microscope system.
Figure 4B:
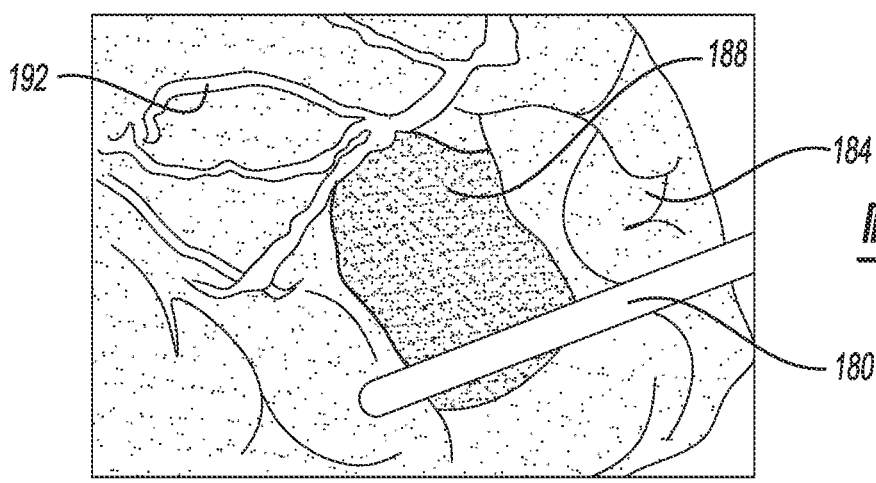
FIG. 4B is a superimposed view through a microscope.
Figure 4C:
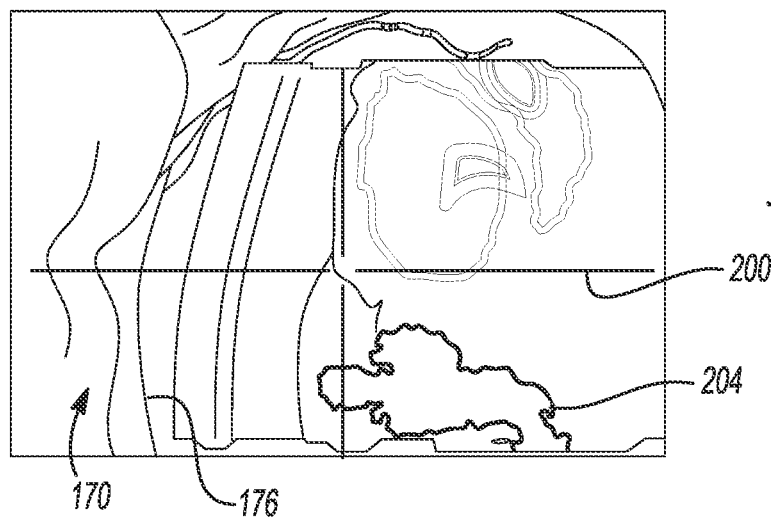
FIG. 4C is a mixed live view and superimposed view through a microscope system.

With continuing reference to FIG. 1 and FIG. 2, and additional reference to FIGS. 4A, 4B, and 4C, a live view 170 through a microscope 32 is illustrated. The live view 170 may allow for viewing selected portions of the subject 34, such as a surface of a brain 174. In addition to the surface of the brain 174, various other items may also be viewed, such as cranial bone 176 and the instrument 34. The eyepieces 44 allow for direct visualization of portions of the subject 34, such as the instrument 110 and/or portions of the subject 34, such as the brain 174 in the live or real time view 170. The direct visualization by the user 80 may be of any items within the visual range of the microscope 32 relative to the subject 34.

As discussed above, the subject 34 may be tracked with the subject tracking device 120 and the microscope 32 may be tracked with the microscope tracking device 118. The instrument 110 may be tracked with the instrument tracking device 112. According to various embodiments, a display, such as a mixed or superimposed view through the eyepieces 44, includes a graphical representation or a graphical overlay in a three-dimensional manner, as illustrated in FIG. 4B. The graphical representation may include a three-dimensional graphical representation 180 of the instrument 110 relative to portions of the subject, such as of a graphical representation of a brain surface 184 and a representation of selected portions or targets 188, such as an identified tumor. Additionally, various anatomical features may also be illustrated in the graphical representation such as vessel structures 192 and/or other anatomical structure of features such as ventricles, fiber tracts, optical nerves, eye balls.

Thus, the display through the eyepieces 44 may be of a three-dimensional representation based upon various information, such as prior acquired image data of the subject 34 and/or graphical representations of the instrument 110, such as the graphical representation 180. The positioning of the various representations, including of the selected target or tumor 188 and/or the instrument representation 180 may be based upon tracking the subject 34 with the subject tracking device 120 and the instrument 110 with the tracking device 112. Accordingly, a three-dimensional representation may be displayed for viewing by the user 80 with the microscope 32 including prior acquired information or information not viewable directly with the microscope 32. While the microscope 32 may provide or allow a magnified view that is a live view of the subject 34, as illustrated in FIG. 4A, the representation of additional information for display relative to the subject 34, such as superimposed and/or displayed with the live image 170, may allow for additional conceptualization or understanding of the subject 34 and/or portions relative thereto by the user 80.

During the surgical procedure, or any appropriate selected procedure, the user 80 may select to display or not display various information, including the three-dimensional representation as illustrated in FIG. 4B. The user may use the input 86 or instruct the inputs 86 (e.g. instructing an assistant, voice controls, or the like) to display or not display various three-dimensional features.

Additionally, and/or alternatively, two-dimensional representations may be displayed superimposed and/or overlaid on the live image 170, as illustrated in FIG. 4C. The live image 170 may display various portions of the subject 34 as illustrated directly or viewed directly through the microscope 32 by the user 80. Thus, the live view may display various portions, such as the bone structure 176 and/or other features. However, displayed or superimposed on the live image may be representations of various structures and/or features, such as a prior identified tumor or target 200 that may be displayed, such as by an outline or indication. Further, various anatomical structures, such as vasculature or skeletal may also be displayed by overlays, such as anatomical overlays 204. Again, the overlays may be displayed relative to the live image 170 due to a registration and/or tracking of the subject 34 and the microscope 32 and registration to the prior acquired image. In various embodiments, the user, or other appropriate user, may identify a selected feature such as anatomical features and/or targets (e.g. a tumor) in prior acquired image data (e.g. magnetic residence imaging (MRI)). The prior acquired and/or determined features may then be registered to the subject 34 during a selected portion of a procedure and superimposed on the live image 170, as illustrated in FIG. 4C. This allows the user 80 to understand or recognize poses of identified features and alternative or additional image (e.g. MRI) for display on the live image 170 of the subject 34. Thus, the user 80 may view both a live image and/or the augmented image to understand the additional features identified in alternative image data.

Again, the user may determine to display or not display various features with the inputs 86 of the microscope system 30. The user may use the microscope 32 to directly view the subject 34 and/or augment the view of the subject 34 during a selected procedure. The additional information may be used by the user 80 to identify and/or understand representations or poses of previously identified or determined features, such as tumors or selected anatomical targets or features.

Figure 5A:
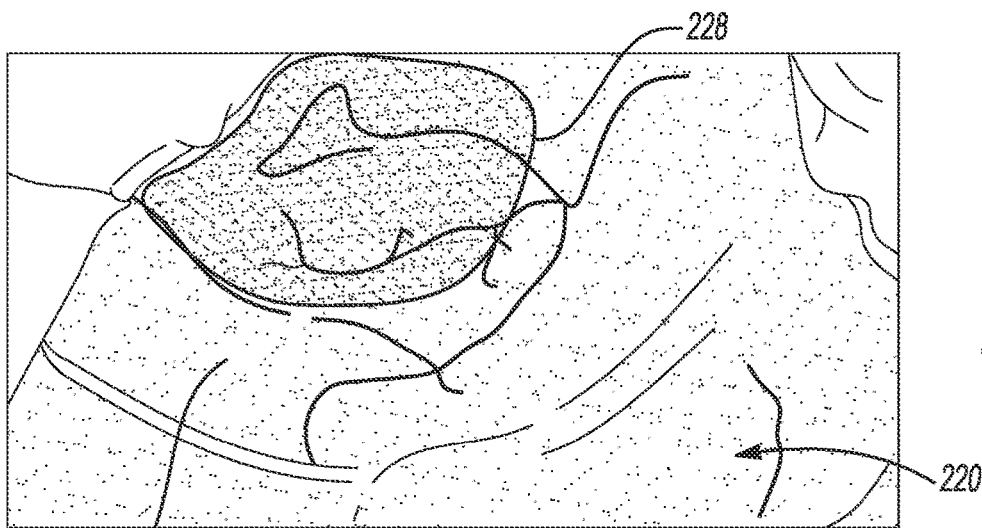
FIG. 5A is a live view and mixed superimposed outline through the microscope system.
Figure 5B:
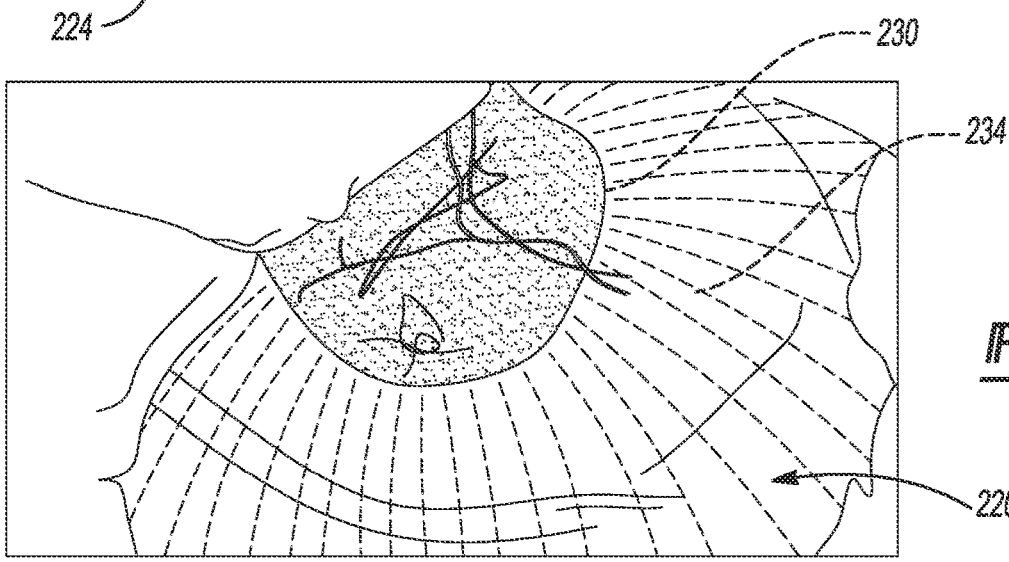
FIG. 5B is a live view of a fluorescent through a microscope system.
Figure 5C:
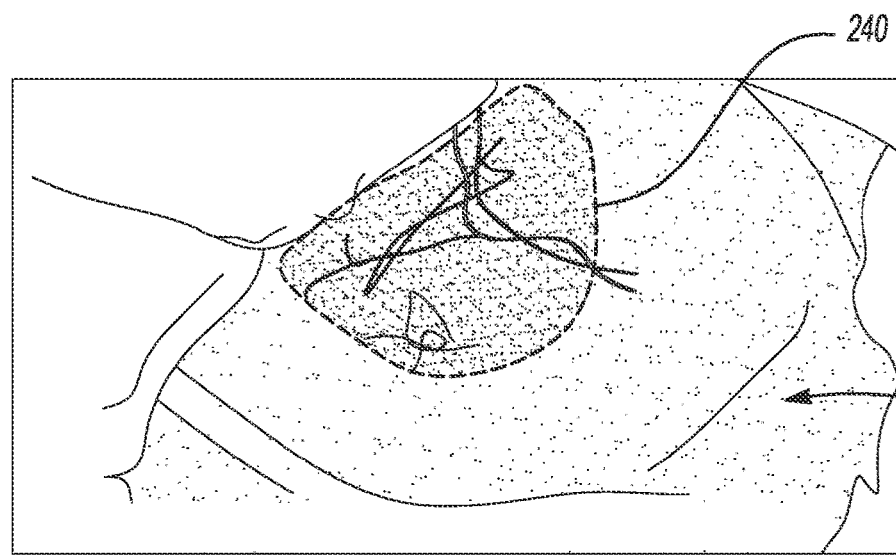
FIG. 5C is a mixed view through a microscope system.

With continuing reference to FIG. 1 and FIG. 2, and additional reference to FIGS. 5A, 5B and 5C, the display or image view by the user 80 may include a substantially live view 220 of the subject 34 including a surface of a selected portion of the subject 224 such as a brain surface. As discussed above, various additional information may be superimposed and/or displayed on the live image 220, such as an outline 228 of a selected target or portion (e.g. a tumor). The target image display 228 may be based on prior acquired or reviewed information, such as MRI data.

During a selected procedure, additional procedures or information may be acquired or utilized. Various digital techniques and/or operative techniques may include fluorescence of selected anatomical features or portions of the subject 34. For example, as illustrated in FIG. 5B, a fluorescent material and/or materials may be provided to the subject 34. Thereafter, the materials may fluoresce and/or may be induced to fluoresce in a selected manner. As illustrated in FIG. 5B, for example, a selected area may have a first fluorescent 230 and a second area may have a second fluorescent 234. The image or view may be the live view 220 of the subject 34 through the microscope and the user 80 may view the selected fluoresce directly. Additionally, the image may be viewed or analyzed by the microscope system 30. The system may identify or distinguish between the high or bright fluorescence 230 and the low fluorescence 234. Based upon differentiation of the fluorescence, the processor system 88 may identify or segment the bright area 230 from the darker area 234. In various embodiments, a high or bright fluorescence 230 region may be referred to as a bright region and may have a brightness or luminescence that is at least about 10% brighter when compared to the low fluorescence 234 region. In various embodiments, the bright region may have a brightness or luminescence at least about 50% brighter, at least about 200% brighter, or about 400% brighter. The bright region may be a two-dimensional area and/or a three-dimensional volume.

The microscope system 30, including the processor, may then segment the view or image of the subject 34 based on the fluorescence. The area or line between the bright fluorescence 230 and the low fluorescence 234 may be determined in any appropriate manner, such as by segmentation. The segmented region, therefore, may be used to determine a current or updated region of volume of the target. The updated region may then be displayed, as discussed herein.

As illustrated in FIG. 5C, therefore, the live view 220 may have overlayed thereon a mixed or augmented outline graphical representation 240 that may be based upon the segmentation of the bright fluorescence area 230 from the darker fluorescence area 234. In various embodiments, for example, the second or augmented outline 240 may be displayed with the fluorescence and/or after the fluorescence has ceased. Thus, it is understood, that the secondary or augmented for representation 240 may also be displayed without the fluorescence. For example, during a selected procedure, fluorescence may occur during illumination of the subject 34 with a selected wavelength of light or energy. At that time, the fluorescence may occur within the subject 34 and the image may be analyzed by the microscope system 30. After analysis of the image, the identification of the augmented outline 240 may be made. The outline may then be displayed for view by the user 80, such as an overlay or superimposing of the outline 240 on the live view 220.

The augmented or updated outline may be used by the user 80 to determine a progress of a selected procedure. For example, during a selected procedure an ablation or removal of a selected portion of the subject may occur, such as removal of a tumor or removing or ending an aneurism. Thus, the user 80 may view the updated outline 240 to assist in determining progression of the procedure. The outline, or any appropriate representation, may therefore allow for a geometry (e.g. shape and size) to be illustrated and changes relative to the initial or first outline or representation 228. This may be in addition to a pose (i.e. x,y,z location and orientation) thereof.

It is understood that the luminescence of the subject 34 may occur more than once and may occur at various times during a procedure. The fluorescence may be used to identify or determine an update or change in the subject anatomy or selected portion thereof. The user, therefore, may understand or better visualize a change in the subject or portion of the subject 34.

In various embodiments, the wavelength of illumination of fluorescents of the selected portion of the anatomy may be in a non-visible wavelength. Accordingly, the fluorescence that may be a bright fluorescence 230 relative to a darker fluorescence 234 may not be visually identifiable by user 80. The microscope system, or appropriate system, however, may analyze the image of fluorescence in the non-visible wavelength to identify the differentiation between portions of the anatomy or subject. Thus, the outline 240 that may be superimposed on the live image 220 may be the only visual representation to the user 80 of a differentiation of fluorescence. Accordingly, the microscope system 30 may be used to display a difference between an initial outline 228 and an updated or second or later outline 240. As discussed above, the initial outline 228 may be based upon prior acquired image or information of the subject 34 such as with image data including MRI image data. A change in the subject or portion of the subject during a procedure may be identified and determined and displayed (e.g. with an augmented outline) for use by the user 80.

Figure 6B:
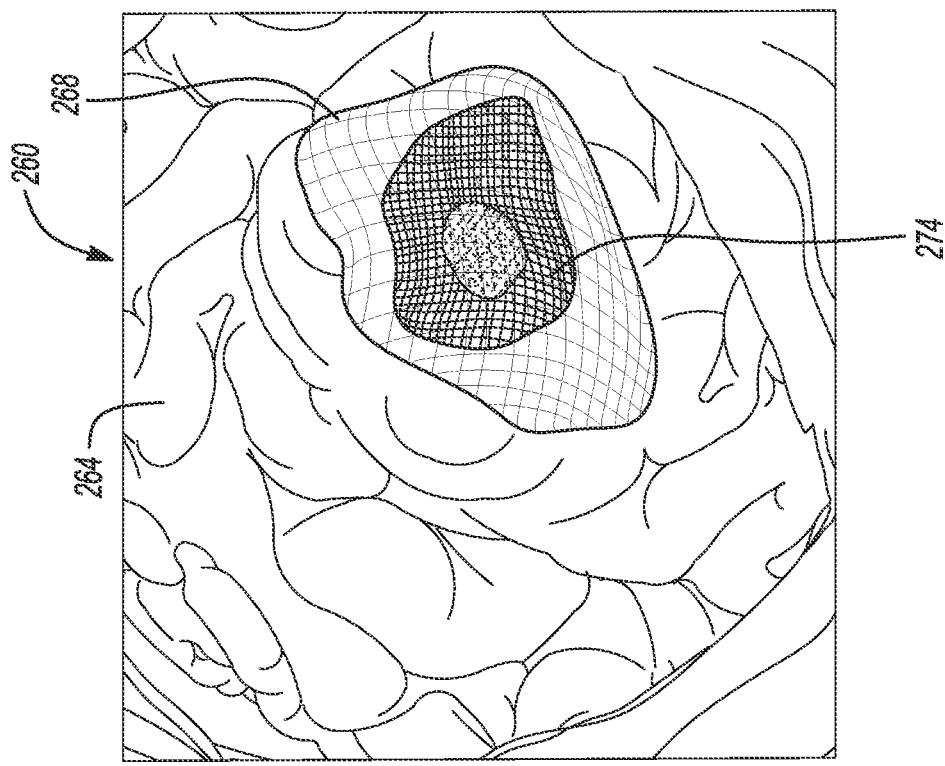
FIGS. 6A and 6B is a mixed live view and changing superimposed graphic.
Figure 6A:
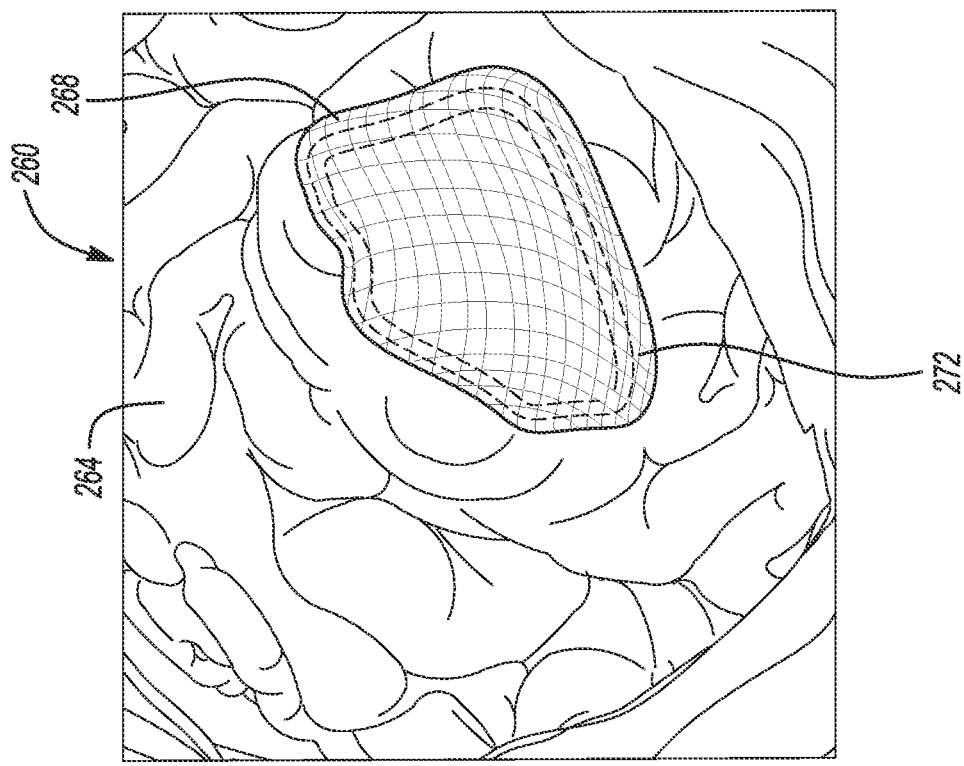

With continuing reference to FIGS. 1 and 2 and additional reference to FIGS. 6A and 6B, a live view image 260 of the subject 34 may include viewing a portion of the subject, such as a brain surface 264 directly. Further, an outline or graphical representation 268 of a selected portion or target, such as a tumor, may also be displayed. The target may be determined or selected in an image or live view in various manners such as by manual determination (e.g. a user outline the target), image segmentation (e.g. automatic segmentation based on selected algorithms such as color or edge detection), and/or recalling a prior determined or delineated target (e.g. accessing and recalling from a memory). As discussed above, the identification of the tumor as that is illustrated as the graphical representation 268 may be based on prior acquired information, such as prior acquired MRI data of the subject 34. The graphical representation 268 may be based upon a registration of the prior acquired image and/or determination of a tumor or target to the subject 34 in part due to tracking the subject 34 with the subject tracking device 120. As also discussed above, additional graphical representations may be displayed relative to the live image 260, but are not displayed here for clarity of the current discussion.

The graphical representation 268 may illustrate a selected or determined boundary of the tumor relative to the live image 260. The live image 260 may be viewed by the user 80 through the eyepieces 44. Accordingly, even a binocular three-dimensional view of the brain surface 264 may be augmented with the graphical representation 268 to illustrate a depth, shape, and the like of the selected target. In addition to a static boundary, however, a pulsing or moving boundary representation 272 may be illustrated. With continuing reference to FIG. 6A and additional reference to FIG. 6B, the live view 260 may illustrate a substantially unchanging or unmoving portion of the subject, such as viewing the brain surface 264 in a fixed location. Also, the static boundary 268 of the selected target or tumor may also be displayed relative to the surface 264 of the brain. The pulsing or changing representation 272 may, however, move or appear to move such as changing a highlighted portion or color of the boundary of the tumor over a period of time. For example, the pulsing shell or grid 272 in FIG. 6A, may illustrate an upper most or closest to the surface boundary of the tumor. At a second time, such as over a period of time of a fraction of a second or numerous seconds (e.g. about 0.1 to about 0.5 seconds) the pulsing grid 272 may change shape and position to a second grid position 274, as illustrated in FIG. 6B.

At a selected time, the user 80 may select to have a geometry of the tumor or target of the subject 34 illustrated in a changing or pulsing manner. Accordingly, a first portion of the pulsing grid 272 may be highlighted or illustrated, in FIG. 6A. In the same view or plane, a change in the highlighted portion of the grid or outline of the tumor, as illustrated by the different or second portion 274 in FIG. 6B. This allows the user 80 to view a dynamic change in a selected portion of the view without moving the microscope 32.

Figure 7:
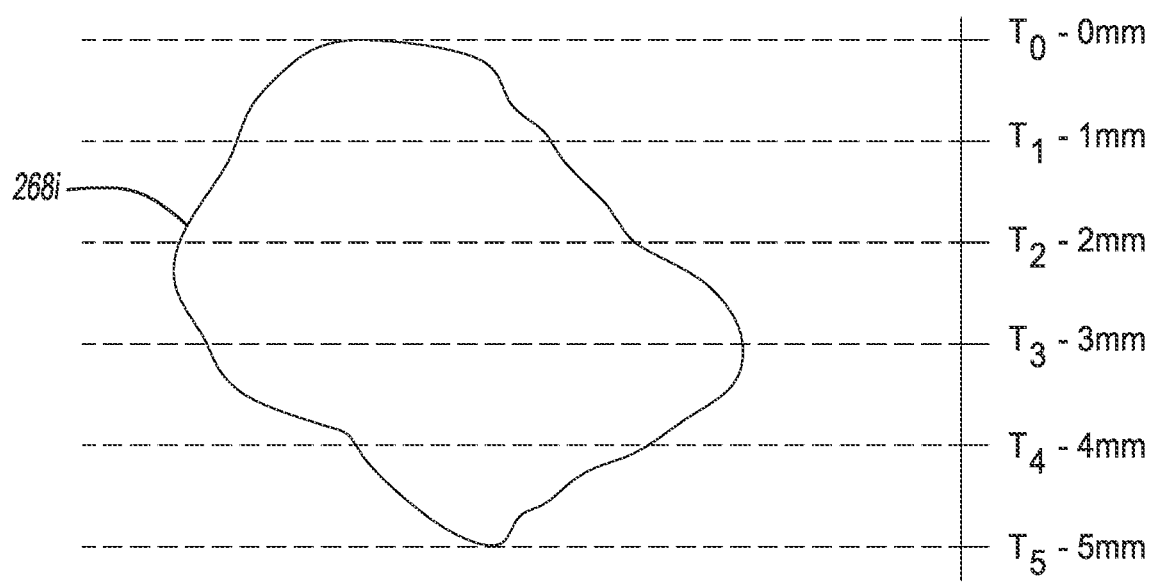
FIG. 7 is a schematic illustration of a target object.

It is understood that any appropriate number of highlighted portions may be illustrated over a selected period of time, such as in sequence. For example, the tumor or target, having the static graphic representation 268, may have a selected depth or exterior geometry, as exemplary illustrated in FIG. 7. During a time zero or at a time zero (T0), the grid shell 272 may illustrate the boundary at a surface or zero millimeter depth into the tumor or target 268i that is graphically represented by the outline 268 in FIGS. 6A and 6B. At selected time periods, such as about 0.1 to about 0.5 seconds apart, an outline at selected depths, such as 1 millimeter depths, may be illustrated by highlighting or changing a color of the grid, for example as illustrated by the different grid portion 274 and illustrated in FIG. 6B. It is understood that any appropriate number of dimensions or times may be used and 1 millimeter dimensions at selected times T0 through T5, as illustrated in FIG. 7, is merely exemplary. Nevertheless, at the selected times, for example, the different portions at T0 through T5 may be sequentially highlighted and illustrated in the display, such as superimposing on the live view 260 for viewing by the user 80.

As the selected portion or different portions of the target, such as the tumor 268i are highlighted, the user 80 may understand the outline of the tumor 268i at a different depth relative to the surface or zero millimeters. Thus, the user 80 may understand an outline or shape of the tumor 268i when viewing the live image 260 with the microscope 32. The pulse geometry outline 272, 274 may be initiated or stopped by the user 80 at selected times to understand the predetermined or identified shape of the tumor 268i. In other words, the user 80 may update the portion or location of the pulsing (e.g. a pulsing plane) to be highlights or designated. Thus, rather than an automatic pulsing, the user 80 may select the portion or plane to be highlighted. The outline or pulsing shape may be displayed for understanding of the target by the user 80 within the subject 34.

Figure 8B:
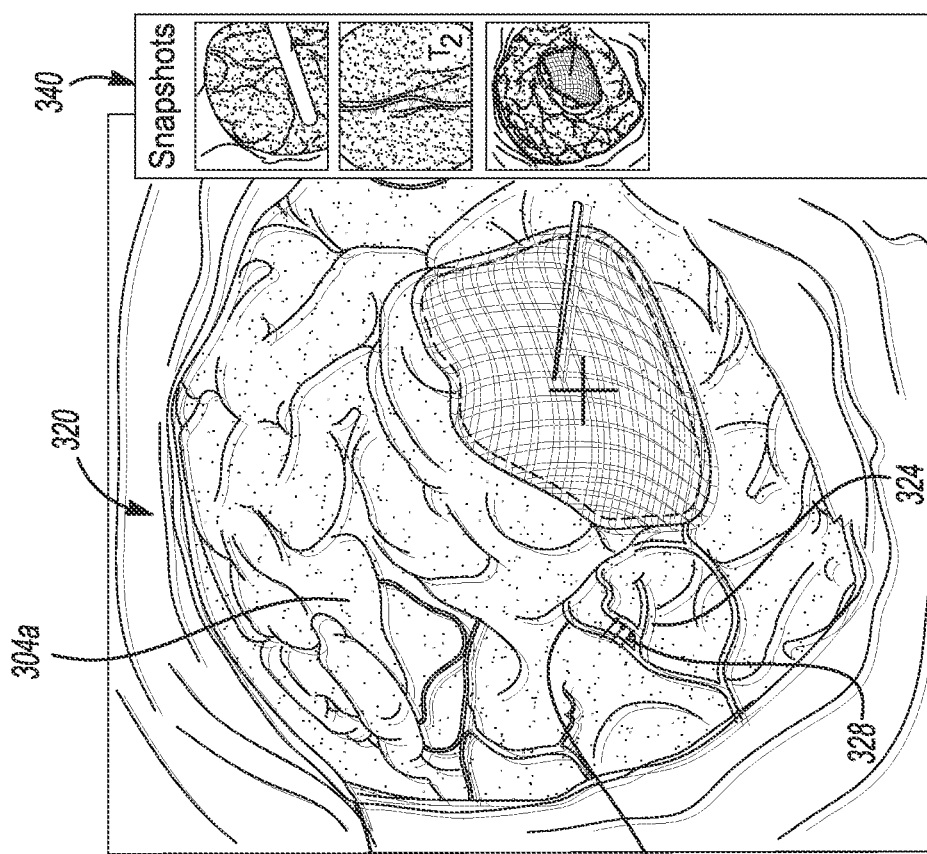
FIG. 8B is a live view and superimposed prior acquired image through a microscope system.
Figure 8A:
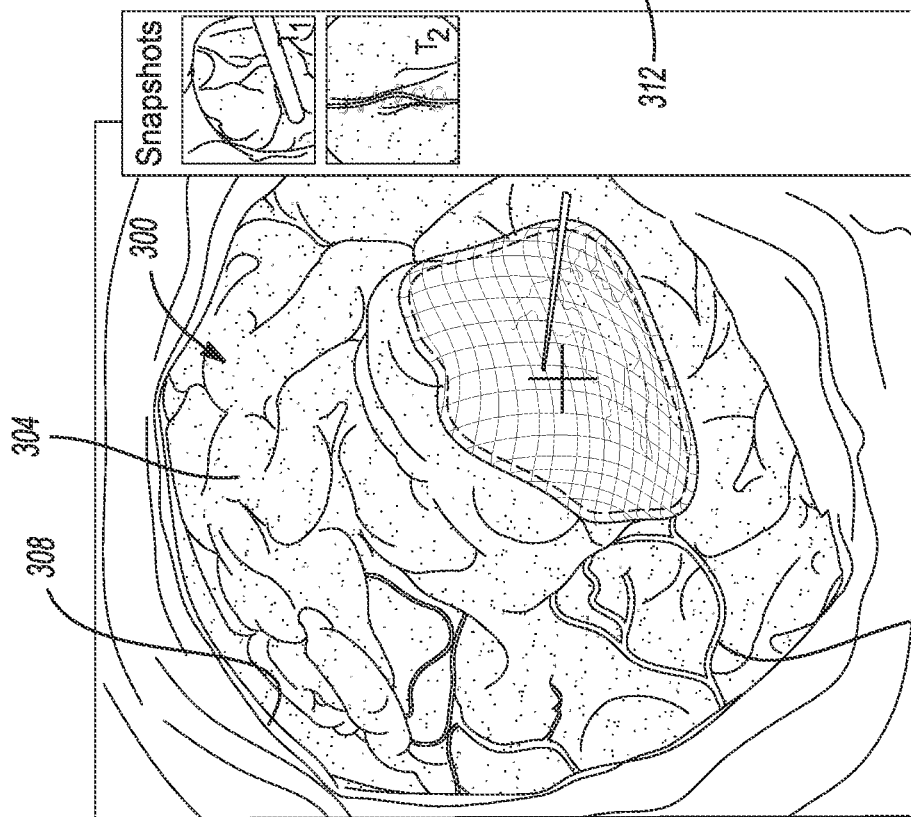
FIG. 8A is a first view at an initial time of the microscope system.

With continuing reference to FIG. 1 and FIG. 2 and additional reference to FIGS. 8A and 8B, the microscope 32 may be used to view a live image 300 of the subject 24, as discussed above. The live image 300 may include various portions, such as a surface 304 of a brain of the subject. In addition to a surface of an organ, such as the brain 304, other features may also be viewed or displayed by viewing through the eyepieces 44 of the microscope 32. For example, a bone structure 308 may be viewed and one or more other soft structures or soft tissues, such as a vasculature including one or more arteries 312. Although the discussion herein, for example with reference to FIGS. 8A and 8B, may refer to the artery 312, it is understood that various features may be displayed and analyzed in addition to the artery 312 as discussed further herein.

As discussed above, the microscope 32 may be fixed relative to the subject 34 and/or tracked relative to the subject 34. In various embodiments, for example, the base stand 70 may be fixed relative to the subject 34 and the subject 34 fixed relative to the microscope 32, such as the head clamp or holding frame 39. Accordingly, the microscope 32 may move relative to the subject 34, such as for obtaining access to portions of the subject 34, viewing more than one area of the subject 34, or other appropriate reasons. As the microscope 32 moves, the eyepiece 44 also moves. Generally, the view of the user 80 is with the eyepiece 44 and movement of the eyepiece 44 may be determined or most relevant relative to movement of the microscope 32. Thus, movement of the microscope 32 may be understood to refer or relate to movement of the eyepiece 44. Regardless, the microscope 32, including the microscope system 30, may be used to obtain images of the subject 34 at various times, such as at a first time and a second time.

During the surgical procedure, the microscope may be moved from a first or original pose at a first time, to a second pose at a second time and then back to the original or first pose at a third or selected time. The various poses of the microscope 32 may be determined due to tracking the microscope 32 with the selected tracking device, including a microscope tracking device 118 and the patient tracking device 120. Further, as discussed above, the selected arms or mechanical robotic portions of the microscope system 30, including the arms 62, 64 may be moved with substantial precision due to the selected motors 74, 76. Regardless, the microscope 32 may be moved from a first pose or an original or for purposes of viewing the subject 32 after a selected period of time.

Accordingly, for example, as illustrated in FIG. 8A, a first view at the first pose of the microscope 32 of the subject 34 may be directly viewed through the microscope 32. At that time, an image or snapshot may be acquired of the subject 34 through the microscope 32. In various embodiments, a camera or image gathering system may be associated with the microscope 32. The image may be stored in a selected memory system, such as the memory 90, for recall at a later time. The image may include various portions, such as the surface 304 of the brain, the bone 308, and the artery 312. Snapshots at selected periods of time, including a first time T1 and a second time T2 may be displayed relative to the row view or live view 300.

With reference to FIG. 8B, therefore, after a selected period of time, such as at a time T3, the microscope may be returned or moved to the pose at time T1. The pose at the T1 time may be determined or saved due to the tracking of the microscope 32. In various embodiments, the robotic arms (including the motors 74, 76) may be used to automatically or upon an input command to move the microscope to a prior pose (i.e. a pose at T1 at which an image was acquired for a snapshot). Accordingly, a live view 320 may be of the subject 34, including a brain surface 304a. Overlaid on the live view 320, including the brain surface 304a may be an image acquired at time T1, as illustrated in FIG. 8A. Due to various analysis of the image and/or identification by the user 80, various vasculature or portions may be identified in the image overlaid on the live view 304a. For example, as illustrated in FIG. 8B, the original pose of the vasculature 312 may be displayed relative to a new or changed pose 324. Further, the microscope system 30 may include indications or arrows 328 to illustrate determined orientation or change in pose of the subject 34, such as the brain surface 304a at the current time relative to the original time for which the overlaid view is made. The arrows 328 may include an original at the original or T1 pose of the selected structure (e.g. vasculature 312) and a head or tip at the current or live view pose of the selected structure (e.g. vasculature 324).

Any appropriate number of prior time snapshots may be displayed or acquired. For example, a plurality of snapshots 340 may be generated at selected times, such as time T1, time T2, and time T3. Each of the snapshots 340 may be displayed overlaid on the live view of the current surface of the brain 304a for viewing by the user 80. Accordingly, the user 80 may select one or more of the snapshots 340 for displaying to augment the current live view of the surface of the brain 304a.

The prior snapshots may be overlaid on the current live view due to the pose of the microscope 32 back at the pose at a prior time, such as the time T1. Accordingly, the change or possible change of selected portions of the anatomy, such as a vasculature, may be viewed and displayed relative to an initial view or a first view acquired during a movement of the microscope 32 at a prior time or first time in a procedure. Regardless, the user 80 may view the live view with an overlay or superposition of a prior acquired snapshot for viewing the results of the change in time and/or a portion of a procedure relative to the subject 34.

With continuing reference to FIG. 1 and FIG. 2, and additional reference to FIGS. 9A and 9B, the user may view the subject 34 with the microscope 32 such as to view a live or real time view 420 of the subject 34. As discussed above, the microscope 32 may be moved by the user 80 in an appropriate manner, such as from a first pose to a second pose. Further, the microscope 32 may be tracked with the tracking system including the localizer 114 microscope tracking device 118 relative to the subject 34 with the subject tracking device 120 or due to various movement determining portions such as those included with the motors 74, 76 and/or included robotic features. In various embodiments, therefore, the user 80 may determine or track a pose or know a pose of the microscope 32 relative to the subject 34. In addition, the user 80 may return the microscope 32 to a prior pose by tracking or saving a pose of the microscope 32 relative to the subject 34. Therefore, the microscope 32 may be used to view the subject 34 at a first time and a second time and make comparisons between the two times, for example as discussed above. In addition thereto, however, the user 80 may also determine or know the pose of the microscope for viewing the subject 32 and analyzing or evaluating poses of selected portions of the subject 32 at different periods of time or over a period of time.

With reference to FIG. 9A, for example, the user 80 may identify various checkpoints or landmarks in the subject 34. For example, with reference to FIG. 9A, the user 80 may identify one or more physical or real landmarks in a live view or view 420 through the microscope. A physical landmark may include a marking (e.g. optical marking), such as an X or ink marking including a first physical landmark 424, a second physical landmark 428, a third physical landmark 432, and a fourth physical landmark 436. The physical landmarks 424-434 may be identified by the user 80 such as identifying a physical landmark in the subject, or placing a physical landmark on the subject, such as the ink markings. The landmarks may be identified by the user 80, such as identifying portions that are illustrated or viewable in an image.

The microscope system 30 may identify the physical landmarks such as through an analysis of the image viewed with the microscope 32. An analysis may include a machine learning algorithm to identify selected features of the physical markings, or other appropriate identification or determination measures. For example, as illustrated in FIG. 9A, the intersection of the two ink marks (i.e. "X") may be used as an indication of a particular finite or fixed checkpoint 424i-434i. The checkpoints may be identified in or to the microscope system 30, such as through an automatic identification, manual identification (e.g. identification by the user 80 to the microscope system 30 with various inputs, including the input 86), or other appropriate determinations.

Further, as discussed above, the microscope system 30 may acquire or determine an image of the subject 34 at a first time. After a selected period of time, such as after one minute, two minutes, or after a selected time based upon a decision of the user 80, a second image or determination of the checkpoints 420-434 may be made. As discussed above the pose of the microscope 32 may be known or determined with the tracking system, including the microscope tracking device 118 relative to the subject 120 and/or due to the robotic or motor mechanism 74, 76 in the microscope system 30. Thus, the microscope 32 may be moved to view the subject 34 at substantially the same pose as during the acquisition of an initial determination of the checkpoints 424-434. This allows an analysis may be made between the initial and current checkpoints.

As illustrated in FIG. 9A, the current checkpoints may be viewed as the physical markings and the prior checkpoints may be indicated as graphical representations, such as by "CP" followed by a number. Further, various indications may be provided regarding the initial checkpoint pose such as a color, indication, or a key, as illustrated in FIG. 9A. Again, the key may be an augmented view through the eyepieces 44 relative to the image 420 displayed for view by the user 80.

Regardless, for example, CP1 may be illustrated in green and the key may indicate that less than one millimeter distance change has been made or determined between a prior pose determination and a current pose determination. Alternatively, or in addition thereto, the CP3 may be indicated as "off plan" or greater than a predetermined or set limit. The additional checkpoints CP3 and CP4 may also be illustrated in selected colors, such as yellow and red respectively, relating to the distance of change between the initial illustration or determination and the current pose. Thus, the microscope system 30 may be used to illustrate an amount of change in pose of the subject 34 from a first time to a current time. In various embodiments, this may be used to determine if a re-registration is necessary and/or may be determined with a re-registration of re-alignment of the microscope.

In various embodiments, for example, the checkpoints may be placed on substantially rigid structures, such as a bone structure 450 of the subject 34. Thus the rigid bone structure may be determined to have moved between a first time and a current time and a re-registration or redetermination of a pose of the subject 34 may be indicated.

Further, various soft tissue or organ poses may also be determined relative to selected checkpoints. For example, with reference to FIG. 9B, the checkpoints 424-434 may be illustrated relative to a soft tissue 460 of the subject 34. Further, various soft tissue portions, such as functional indications may be illustrated including a first function pose 464 and a second function pose 468. The function poses 464, 468 may be illustrated or marked on the brain 460 with an appropriate marking such as a bio-compatible marker or physical portion. Additionally, due to a determined or trackable pose of the microscope 32 relative to the subject 34, the functional poses 464, 468 may be illustrated as superimposed portions or features on the brain 460 for viewing by the user 34 in the view 470. Thus, the live view 470 may have superimposed thereon indications of the functional poses 464, 468.

The functional poses 464, 468 may be determined due to probing of the brain 460 by the user 80. Accordingly, the functional poses 464, 468 may not include physical or identifiable landmarks on the brain 460, but may be based upon functional indications determined by the user 80. Nevertheless, the microscope system 30 may view the functional poses 464, 468 relative to the checkpoints 424, 434. The functional poses 464, 468 may be displayed as graphical representations to the user 80, however.

A determination of movement or lack of movement may be used to determine whether there has been brain shift of the brain 460 relative to the fixed or rigid portions, such as bone 450, of the subject 34. For example, the microscope system 30, in a manner similar to that discussed above, may identify or determine the checkpoint poses 424-434. The functional poses 464, 468 may then be determined relative to the checkpoints 424-434 at a first time and a second time, or a time later than the first time. An indication of movement or no movement, therefore, may also then be made to the user 80 in the view.

For example, relative to the live view 470, an augmented portion, including a key, may be viewable by the user 80 through the eyepieces 44. For example, the numbers 1 and 2 may be used to identify the different functional poses 464, 468, respectively, and an indication of whether they are on or a distance relative to an initial pose may be made. The key may indicate that functional point 1 is on the same or similar pose and functional point 2 is at a distance greater than two millimeters relative to the initial pose. Thus, the user may identify or understand the current pose, including, if present, amount of change to the current pose of the brain 460 relative to the checkpoint between two periods of time. Again, therefore, the user 80 may then determine whether a procedure may continue or be augmented due to a possible shift of the brain 460. Further, a determination of a pose of the functional point may be reevaluated based upon indication of possible change.

Figure 10:
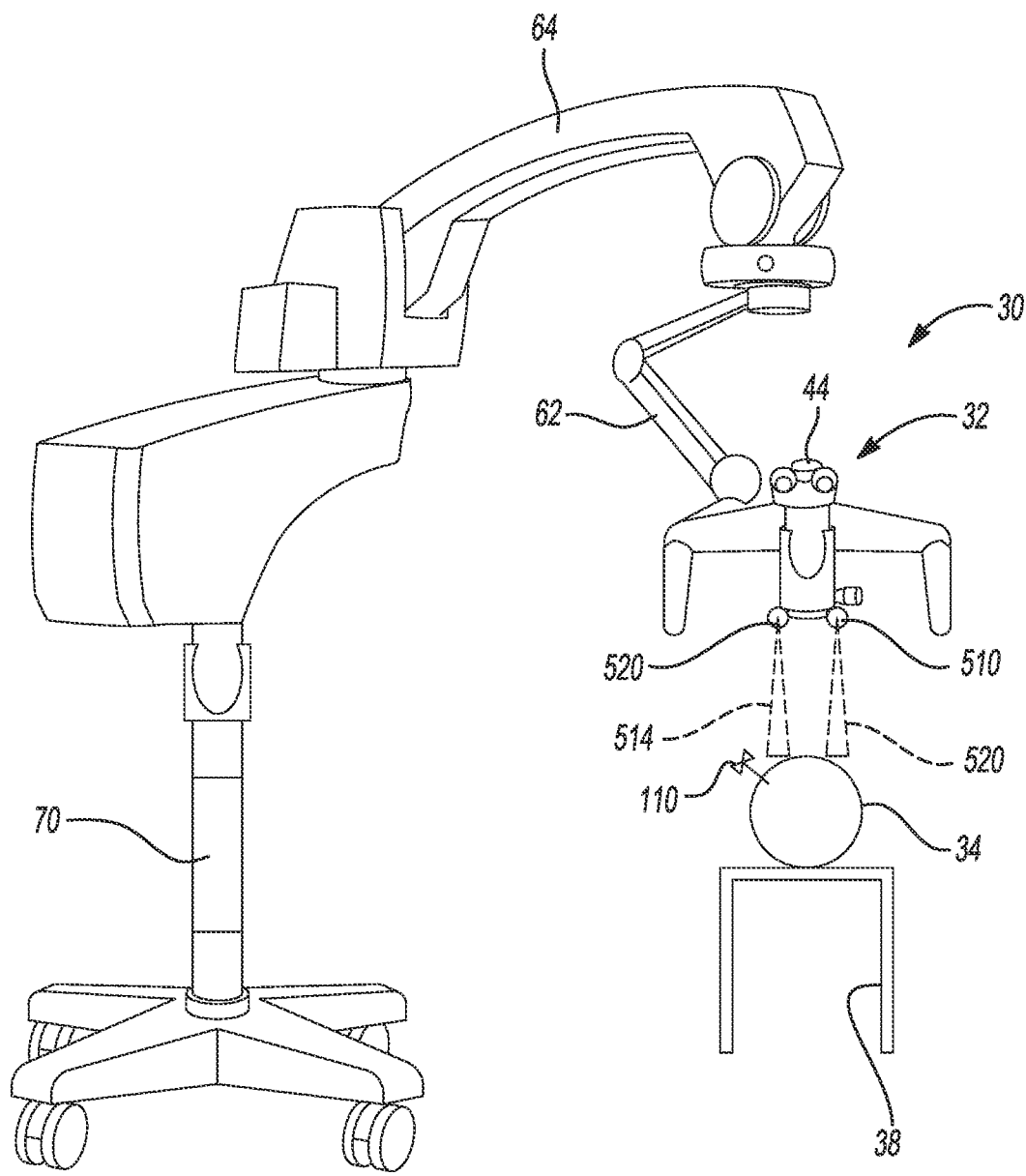
FIG. 10 is a microscope system with a range finding portion.

With continuing reference to FIG. 1 and FIG. 2 and additional reference to FIG. 10, the microscope may include additional or alternative tracking or locating the systems in addition to the tracking device 118 associated with the microscope 32, as illustrated in FIG. 2, or other portions. For example, a relative range finding system may include one or more range finders such as a first range finding system or portion 500 and a second range finding system or portion 510. Each of the respective range finding portions 500, 510 may project or include range finding beams or features 514, 520, respectively. The beams 514, 520 may be signals (e.g. light or acoustic signals) that are sent and received for range finding. The range finding system may be any appropriate systems, such as determining a linear distance or determining a three-dimensional (3D) scan and related distances, and/or etc.

The range finding features 514, 520 may be emitted toward the subject 34 that is supported on a selected support structure, such as the support 38. The range finding features 500, 510 may be incorporated into the microscope 32 and/or mounted to the microscope 32. Accordingly, the range finding portions 500, 510 may be removably mounted to the microscope 32 for a selected procedure and/or portion of the procedure.

The range finding features 514, 520 that may be emitted and/or received by the range finding portions 500, 510 may be selected range finding features such as optical range finding features. In various embodiments, for example, the range finding portions 500, 510 may form or be incorporated into a binocular or three-dimensional imaging range finding system that may triangulate a pose (including distance) relative to the respective range finding portions 500, 510 and the microscope 32 to which they are fixed. In various embodiments, for example, the range finding portions 500, 510 may generate or develop an image of the subject 34, such as a brain portion thereof, to determine a pose of the microscope 32 relative to the subject 34 (and/or a portion thereof), or determine movement of the subject 34, such as a brain therein, relative to the microscope 32 due to a known or fixed pose of the microscope 32 relative to a portion of the subject 34 and/or the support 38.

The ranging or range finding portions 500, 510 may also be other appropriate range finding features such as optical (visible and infrared), acoustic, an ultrasound ranging system, radar ranging system, or other appropriate ranging system. Regardless, the ranging system may be incorporated into the microscope 32 and/or affixed to the microscope 32 for a selected procedure or a portion of a procedure. Thus, the ranging system 500, 510 may be used to identify pose of the microscope 32 relative to the subject 34 and/or pose of portions of the subject 34 relative to other portions (e.g. brain shift).

In various embodiments, the ranging system portions 500, 510 may emit the respective beams 514, 520. The beams 514, 520 may reflect off of the subject 34 or portions thereof. The reflected portions may be received by the ranging system portions 500, 510 or other appropriate portions. The emission and receiving may be used to determined pose of the subject 34 relative to the microscope 32 including the ranging system portions 500, 510. As noted above, the pose of the instrument 110 may also be determined relative to the microscope 32 and the subject 43.

Further, the ranging system portions 500, 510 may include various features such as voice activation or controls. For example, the user 80 may provide an audible input or command to range or determine an amount of brain shift, pose of the microscope or pose of a view relative to the microscope relative to the subject 34, or the like. Thus, the user 80 may interact and provide selected input to the range finding system 510, 520.

Also, the microscope 32 may also view the instrument 110 that may be moved relative to the subject 34. Thus, the ranging system 500, 510 may determine a pose of at least a portion of the instrument 110 relative to the subject 34 and be able to view or display the information in the view through the view finders 44 of the microscope 32. Accordingly, the range finders 500, 510 may be used to range find relative to selected portions of the subject 34 and/or the instrument 110 relative to the microscope 32. The information may be displayed for viewing by the user 80 in the view ports or eyeholes 44, such as for determination of a pose or movement of the subject 34 and/or pose or determination of a pose of the instrument 110.

Accordingly, as discussed above, the microscope system 30 may be used to provide information to the user 80 to assist in a selected procedure. Pose of instruments, such as the instrument 110, and/or overlays may be displayed in the eyepieces 44 for viewing by the user 80. The superimposed information (e.g. target location or dimensions, tracked instruments) may be viewed by the user 80 while the user 80 views the subject 34 through the eyepieces 44. Thus the user 80 may include a view of the subject 34 simultaneously with additional information that may be acquired separately from the microscope 32 and/or prior to use of the microscope 32. The microscope system 30 may allow for the user 80 to provide inputs for selection and/or determination of various features such as poses of instruments, selected targets or identified features (e.g. tumors, anatomical structures, etc.). The user 80 may therefore view directly the subject 34 and/or additional information relative to the subject 34 that may be acquired or determined separate from the microscope or microscope system 30.

As discussed above, according to various embodiments, an image may be viewed with the microscope 32 through the eyepieces 44. The image viewed through the microscope may include a live or real view of the subject, also referred to as a real time view. The live view may be produced by direct visualization of the subject 34. As discussed above the direct visualization may occur due to reflected light or direct light being transmitted through the optics of the microscope 32, such as through the objective lens 52, through internal optics, and finally through the eyepieces 44. Thus, the live view viewed by the user 80 may be of the subject 34 in real time. Further, as discussed above, various additional or augmented or mixed view information may be displayed superimposed on the live view and/or near or adjacent to the live view. Accordingly, the view of the user 80 though the eyepieces 44 may be a mixed view including both the live view of the subject 34 and/or additional information displayed relative thereto. In addition, as discussed above, various views may be displayed to be superimposed on the live view to substantially obscure the live view, such as three-dimensional representation of the subject 34.

Further, as discussed above, the microscope 32, included with the microscope system 30, may be a robotic microscope that may be moved or controlled with the various motors, such as the motors 74, 76 and associated with (e.g. housed in) the respective arms or members 62, 64. Thus, the microscope system 30 may be positioned near the subject 34 and moved in a substantially precise and known manner relative to the subject 34. Alternatively and/or in addition thereto, the microscope 32 may be tracked relative to the subject 34 with a selected tracking system, including the localizer 114. Further, as discussed above, the tracking system may track the subject and/or the instrument 110 in addition and/or alternatively to the range finding system including the range finding portions 510, 520.

Accordingly, the position of the subject 34 may be known relative to the microscope 32, including a view plane of the microscope 32. Thus, the various information may be displayed for viewing by the user 80 through the eyepieces 44 to represent poses, such as depths, orientations, and the like, of instruments and/or portions relative to the subject 34 (e.g. a target including a tumor) due to the known position of the microscope 32 relative to the subject 34 and/or the instrument 110.

Figure 11:
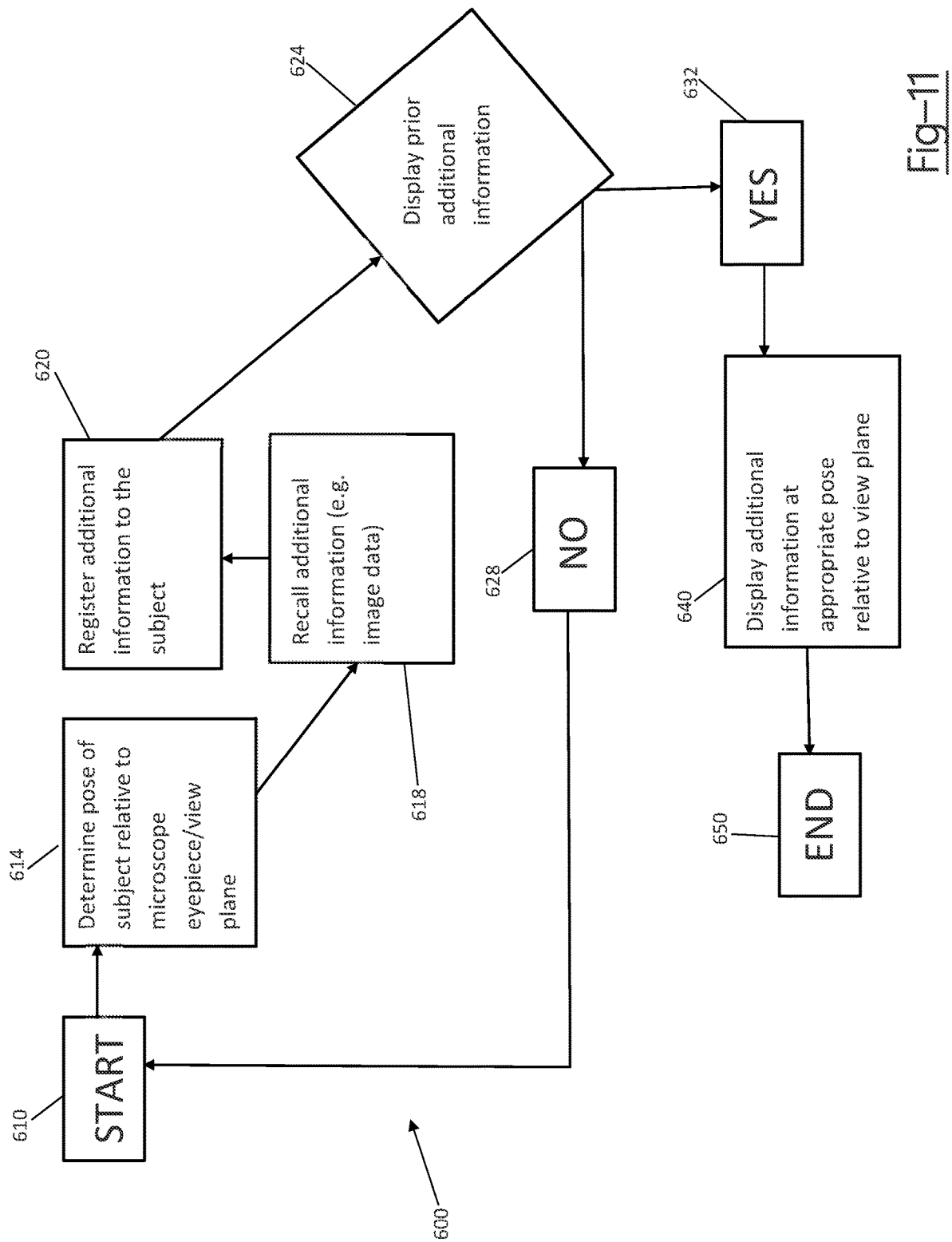
FIG. 11 is a process for displaying prior acquired information.

With reference to the above figures, and additional reference to FIG. 11, a method or process 600 may be used to identify or determine the position of the additional information relative to the subject 34 for display to be viewed by the user 80 with the eyepieces 44. Additional information may be prior acquired image data or other data, such as tractography. Generally, the additional data would be information not viewable in the live view with an optical microscope.

The process 600 may begin in start block 610. After starting the process in block 610, various steps or procedures may occur to determine the position of the subject 34 relative to other acquired information. For example, a determination of a pose of the subject relative to the microscope eyepiece and/or view plane in block 614 is determined. As discussed above, the pose of the microscope 32 and/or the eyepiece 44 and/or a view plane of the microscope 32 may be determined. The pose of the microscope 32 relative to the subject 34 may be determined by determining an initial position of the microscope relative to the subject 34 and/or tracking the microscope relative to the subject 34. Various tracking systems, as discussed above, can be used to track or determine a pose of the microscope 32 at an appropriate time. For example, at a first time or time T1 a pose of the microscope 32 may be determined relative to the subject 34 such as with a robotic system, including a motor 74, 76 and related sensors or encoders and/or the tracking device 118. A later movement of the microscope 32 may also be tracked using the similar systems to determine a second or later pose of the microscope 32 relative to the subject 34.

At an appropriate time, and not required to be after the determination, of the pose of the subject relative to the microscope in block 614, additional information may be acquired in block 618 and a registration of prior acquired information may be made relative to the subject in block 620. The additional information may be any appropriate information, such as prior acquired image data or other appropriate data. The additional information may be stored for recall from a selected memory system, such as the memory 90. The additional information may also, however, be generated substantially in real time such as illustrating or identifying functional locations on the brain.

The additional information may include information acquired with an imaging system prior to the subject being moved relative to the microscope 32, an image acquired with the microscope 32 (e.g. an optically acquired image), tractography data, or the like. As discussed above, the pose of the subject 34 may be determined, such as by tracking the subject 34 with the range finding system and/or the tracking device 120. Further, registration may be made between acquired images and a live view or view with the microscope 32 according to generally known techniques, such as identify landmarks in the subject 34 and identifying similar landmarks or identical landmarks in the prior acquired image.

As discussed above, images acquired with the microscope 32 may include markings therein that may be identified and may later be compared to the same positions on the subject 34 for a determination of possible movement of the subject 34 relative to the initial pose of the subject 34. Similarly and/or alternatively prior acquired images may be registered to the subject 34 for illustrating appropriate portions identified in prior acquired image data (and/or appropriate other data) relative to the subject 34 for viewing with the microscope 32. Thus, the registration of acquired information may be made to the subject 34 at any appropriate time, such as after tracking or registering the subject 34 relative to the microscope 32 and/or registering the subject 34 to the prior acquired image data in the navigation space which may include movement and/or volume for moving of the instrument 110 and/or the microscope 32. Regardless, the registration of the prior acquired information in block 620 may allow for a determination of an appropriate pose of the information in the prior acquired information to the subject 34 during a procedure.

The registered additional information may then be determined whether to be displayed relative to the live view of the subject, such as through the eyepieces 44, in block 624. As discussed above the microscope system 20 may include various inputs that allow for selections by the user 80. Accordingly, the user 80 may use the inputs 86 to determine whether acquired information should be displayed. If a determination that no information should be displayed a NO block or path 628 may be followed to the start block 610. Thus, the determination of a pose in block 614 and registering of information in block 620 may not be required to be displayed for viewing by the user 80.

If, however, the determination is made to display the additional information, a YES path 632 may be followed. After following the YES path 632, a display or illustration of the additional information at the appropriate pose relative to the view plane may be made in block 640. As discussed above, the view plane may be viewed by the user 80 of the subject 34. Accordingly, the additional information may be displayed relative to the view plane for appropriate representation to the user 80.

For example, as discussed above, a tumor or target may be identified in a prior acquired information that may be substantially below a surface of the exterior portion of the subject 34, such as an external surface of the brain. Accordingly, a presentation, such as a graphical representation, of the tumor may be displayed relative to the view plane at the appropriate pose (including depth) for representing the appropriate pose of the tumor for viewing by the user 80 relative to the view pane through the eyepieces 44. The determination of the appropriate pose may be based upon the registration of the prior acquired information to the subject 34 and/or the determined pose of the subject relative to the microscope eyepiece or view plane in block 614. Determining the pose of the plane relative to the subject 34 may allow for an appropriate illustration of the prior acquired information at the appropriate pose relative to the subject 34.

Following displaying 640, the process 600 may end in block end block 650. Ending the process in block 650 may include termination of a procedure, moving the microscope 32 (including, if selected, the surgical microscope system 30), determining an additional information to displayed, or restarting the process 600. Accordingly, the end block 650 may be understood to be an ending of a particular portion of a procedure, such as the displaying of a selected prior acquired information according to the process 600.

The microscope system 30 may be used to display appropriate information for viewing by the user 80. The information may be displayed based upon a determination of a pose of the microscope 32 relative to the subject 34 and a registered or known pose of the prior acquired information relative to the subject 34. This allows the prior acquired information to provide appropriate information in perspective to the user 80 due to displaying the appropriate pose of the prior acquired information to the subject 34.

The information may be displayed as a graphical representation of various portions, such as an instrument, a target (e.g. tumor or anatomical portion), identified feature or portion, etc. The graphical representation may be overlaid on a live image, as discussed above. The graphical representation, according to various embodiments may be fully opaque, partially opaque, or transparent. A fully opaque graphical representation may completely obscure the live image or any portion over which it is overlaid. A partially opaque graphical representation allows for viewing, at least partially, the portions of the live image over which it is overlaid. A transparent graphical representation may include, for example, only an outline and allow for viewing of the live image within the outline.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium (e.g. memory module) and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors (e.g. processor module), such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of generating a display for viewing a subject in a view through an eyepiece of a microscope, comprising:
   determining a first pose of a viewing plane viewed through the eyepiece relative to the subject;
   acquiring a first image of the subject at the viewing plane at the first pose at a first time as viewed through the eyepiece relative to the subject;
   storing the first image;
   displaying the first image in the view plane superimposed on a live image of the subject at a second time as viewed through the eyepiece relative to the subject;
   determining whether a change in position of the live image relative to the first image has occurred; and
   outputting a determination of the evaluation of whether a change in pose has occurred including superimposing a graphical representation indicating an amount of movement that has occurred between the first time and the second time.

2. The method of claim 1, further comprising:
   analyzing the first image; and
   analyzing the live image.

3. The method of claim 2, further comprising outputting the determination, wherein outputting the determined pose comprises:
   generating a graphical representation illustrating the determined change; and
   displaying the graphical representation superimposed on the live image.

4. The method of claim 3, wherein the graphical representation is partially opaque to allow viewing of the live image through the graphical representation.

5. The method of claim 3, wherein the graphical representation includes an arrow having an origin at a point in the displayed first image and a head at a point in the live image indicating a direction and extent of movement of the subject relative to the viewing plane.

6. The method of claim 1, further comprising:
   tracking a head of the microscope relative to the subject with the viewing plane at the first pose;
   tracking a pose of the subject; and
   tracking a pose of an instrument;
   wherein the tracking of the head, subject, and instrument are conducted simultaneous and with a navigation system.

7. The method of claim 6, further comprising:
   comparing the live image at the second time to the first image after moving the head from and returning the head to the viewing plane at the first pose.

8. The method of claim 6, wherein tracking the head includes tracking a head tracking device relative to the subject;
   wherein the head includes an object lens configured to receive light from the subject.

9. A method of illustrating movement in a view through an eyepiece of a viewing system, comprising:
   identifying a landmark on a rigid portion of a subject in a viewing plane viewed through the eyepiece at a first time;
   identifying the landmark on the subject in the viewing plane viewed through the eyepiece at a second time after the first time;
   evaluating whether a change has occurred in the landmark viewed through the eyepiece between the first time and the second time;
   outputting a determination of the evaluation of whether a change is pose has occurred including superimposing a graphical representation indicating an amount of movement that has occurred between the first time and the second time.

10. The method of claim 9, wherein superimposing the graphical representation includes: illustrating with a first graphical representation of the identified location of the landmark at the first time; illustrating with a second graphical representation of the identified location of the landmark at the second time; wherein the second graphical representation is visually distinct from the first graphical representation to indicate at least one of a change in pose or geometry or an amount of change in pose or geometry.

11. The method of claim 9, further comprising:
    forming the landmark on the subject.

12. The method of claim 9, wherein the landmark is a first landmark, further comprising:
    identifying a second landmark relative to the first landmark, wherein the second landmark is on a non-rigid portion of the subject;
    determining a first pose of the first landmark relative to the second landmark at a first time;
    determining a second pose of the first landmark relative to the second landmark at a second time;
    evaluating whether a change in pose has occurred between the first landmark and the second landmark between the first time and the second time;
    outputting a determination of the evaluation of whether a change in pose has occurred.

13. The method of claim 12, wherein identifying the second landmark include identifying a function position in a brain of a subject.

14. A system for determining a pose of a microscope relative to a subject, comprising:
    an eyepiece of the microscope for viewing a view plane;
    a first emitter configured to be connected with the microscope;
    a first receiver configured to be connected with the microscope;
    a processor system configured to communicate with both the first emitter and the first receiver;
    wherein the first emitter is configured to emit a first signal that is reflected from the subject and received by the first receiver;
    wherein the processor system is configured to execute instructions to determine information of a pose of a first portion of the subject based on the emitter and received first signal;
    wherein the information is viewed through the eyepiece of the microscope;
    wherein the processor system is further configured to execute instructions to,
    identify a first landmark;
    identifying a second landmark relative to the first landmark, wherein the second landmark is on a non-rigid portion of the subject;

determining a first pose of the first landmark relative to the second landmark at a first time;

determining a second pose of the first landmark relative to the second landmark at a second time;

evaluating whether a change in pose has occurred between the first landmark and the second landmark between the first time and the second time; and outputting a determination of the evaluation of whether a change in pose has occurred.

15. The system of claim 14, wherein the signal includes infrared radiation.

16. The system of claim 14, further comprising:

a second emitter configured to be associated with the microscope;

a second received configured to be associated with the microscope;

wherein the processor system is further configured to communicate with both the second emitter and the second receiver;

wherein the second emitter is configured to emit a second signal that is reflected from the subject and received by the second receiver;

wherein the processor system is configured to execute further instructions to determine the pose of a second portion of the subject based on the emitter and received second signal.

17. The system of claim 16, wherein the first portion of the subject is spaced apart from the second portion.

18. The system of claim 16, wherein at least one of the first signal of the second signal is operable to reflect from an instrument;

wherein the processor system is configured to execute further instructions to determine a pose of the instrument relative to at least one of the microscope or the subject.

* * * * *